(12) United States Patent
Albizati et al.

(10) Patent No.: US 9,683,001 B2
(45) Date of Patent: Jun. 20, 2017

(54) PROCESS OF PRODUCING PHOSPHINOTHRICIN EMPLOYING NITRILASES

(71) Applicant: Strategic Enzyme Applications, Inc., San Diego, CA (US)

(72) Inventors: Kim F. Albizati, San Diego, CA (US); Spiros Kambourakis, San Diego, CA (US); Alan Grubbs, San Diego, CA (US); Bennett C. Borer, San Diego, CA (US)

(73) Assignee: Stragegic Enzyme Applications, Inc., San Diego, CA (US)

( * ) Notice: Subject to any disclaimer, the term of this patent is extended or adjusted under 35 U.S.C. 154(b) by 7 days.

(21) Appl. No.: 14/638,766

(22) Filed: Mar. 4, 2015

(65) Prior Publication Data
US 2015/0239917 A1    Aug. 27, 2015

Related U.S. Application Data

(62) Division of application No. 13/640,833, filed as application No. PCT/US2010/031007 on Apr. 14, 2010, now Pat. No. 8,981,142.

(51) Int. Cl.
| | |
|---|---|
| *C07F 9/30* | (2006.01) |
| *C07F 9/32* | (2006.01) |
| *C12P 41/00* | (2006.01) |
| *C12P 13/04* | (2006.01) |
| *C07F 9/36* | (2006.01) |
| *C12P 13/00* | (2006.01) |
| *C12P 17/00* | (2006.01) |
| *C12N 9/78* | (2006.01) |
| *C12P 13/02* | (2006.01) |

(52) U.S. Cl.
CPC ............ *C07F 9/3211* (2013.01); *C07F 9/301* (2013.01); *C07F 9/36* (2013.01); *C12N 9/78* (2013.01); *C12P 13/001* (2013.01); *C12P 13/02* (2013.01); *C12P 13/04* (2013.01); *C12P 17/00* (2013.01); *C12Y 305/05001* (2013.01)

(58) Field of Classification Search
CPC ............... C07F 9/30; C07F 9/32; C12P 41/00
See application file for complete search history.

(56) References Cited

U.S. PATENT DOCUMENTS

| | | |
|---|---|---|
| 4,168,963 A | 9/1979 | Rupp et al. |
| 4,518,538 A | 5/1985 | Gehrmann et al. |
| 4,692,541 A | 9/1987 | Zeiss et al. |
| 5,051,525 A | 9/1991 | Willms |
| 5,756,346 A | 5/1998 | Willms et al. |
| 5,756,800 A | 5/1998 | Willms et al. |
| 5,879,930 A | 3/1999 | Willms et al. |
| 6,359,162 B1 | 3/2002 | Willms |
| 6,936,444 B1 | 8/2005 | Bartsch et al. |
| 2009/0111148 A1 | 4/2009 | Dicosimo et al. |

FOREIGN PATENT DOCUMENTS

| | | |
|---|---|---|
| EP | 0382113 A1 | 8/1990 |
| EP | 0690133 A1 | 1/1996 |
| FR | 2829490 A1 | 9/2001 |
| WO | 9504828 A1 | 2/1995 |
| WO | 9909039 A1 | 2/1999 |
| WO | 2007052169 A2 | 5/2006 |
| WO | 2008106662 A2 | 9/2008 |

OTHER PUBLICATIONS

Arosio, D., et al., "Chemo-Enzymatic Dynamic Kinetic Resolution of Amino Acid Thioesters," 2007, Adv Synth Catal, 349:1345-1348.
Bartsch, K., et al, "Stereospecific Production of the Herbicide Phosphinothricin (Glufosinate ): Purification of Aspartate Transaminase from Bacillus Stearothermophilus, Cloning of the Corresponding Gene, aspC, and Application in a Coupled Transaminase Process," 1996, App Environ Microbiol, 62/10:3794-3799.
Berlicki, L., et al., "Design, Synthesis, and Activity of Analogues of Phosphinothricin as Inhibitors of Glutamine Synthetase," 2005, J Med Chem, 48:6340-6349.
Chaplin, J.A., et al., "Chemoenzymatic Approaches to the Dynamic Kinetic, Asymmetric Synthesis of Aromatic Amino Acids," 2004, Tetrahedron: Asymm, 2793-2796.
Engel, R., "Chapter 2. Phosphorus Addition at sp2 Carbon," 1988, Organic Reactions, 36:174-248.
Jessop, C.M., et al., "Radical Addition Reactions of Phosphorus Hydrides: Tuning the Reactivity of Phosphorus Hydrides, the Use of Microwaves and Horner-Wadsworth-Emmons-Type Reactions," 2006, Eur J Org Chem, 1547-1554.
Keller, V., "Dynamic Kinetic Resolution: Practical Applications in Synthesis," Nov. 1, 2001, 36 pages.
Logusch, E.W., et al., "Synthesis of α- and γ-Alkyl-Substituted Phosphinothricins: Potent New Inhibitors of Glutamine Synthetase," 1988, J Org Chem, 53:4069-4074.
Martinkova, L., et al., "Nitrile- and Amide-Converting Microbial Enzymes: Stereo-, Regio- and Chemoselectivity," 2002, Biocatal Biotransform, 20/2:73-93.
Mukherjee, C., et al., "Enzymatic Nitrile Hydrolysis Catalyzed by Nitrilase ZmNIT2 From Naize. An Unprecedented β-Hydroxy Functionality Enhanced Amide Formation," 2006, Tetrahedron, 62:6150-5154.
Rustler, S., et al., "Conversion of Mandelonitrile and Phenylglycinenitrile by Recombinant *E. coli* Cells Synthesizing a Nitrilase from Pseudomonas Fluorescens EBC191," 2007, Enz Microbial Tech, 40:598-606.
Sakakura, T., et al., "Hydroformylation-Amidocarbonylation of Methylvinylphosphinate. Application to Synthesis of Glufosinate," 1991, Bull Chem Soc Jpn, 64:1707-1709.
Tan, S., et al., "Herbicidal Inhibitors of Amino Acid Biosynthesis and Herbicide-Tolerant Crops," 2006, Amino Acids, 30:195-204.

(Continued)

Primary Examiner — Nyeemah A Grazier
(74) Attorney, Agent, or Firm — Senniger Powers LLP

(57) ABSTRACT

The present invention generally relates to processes for the enzymatic production of a phosphinothricin product or precursor thereof from a nitrile-containing substrate.

9 Claims, 2 Drawing Sheets

(56) References Cited

OTHER PUBLICATIONS

Tauber, M.M., et al., "Nitrile Hydratase and Amidase from Rhodococcus Rhodochrous Hydrolyze Acrylic Fibers and Granular Polyacrylonitriles," 2000, App Environ Microb, 66/4:1634-1638.
Wang, L.J. et al., "Enhancement of the Activity of L-Aspartase from *Escherichia coli* W by Directed Evolution," 2000, Biochem Biophys Rsch Comm, 276:346-349.
Dingwall, J.G., et al., "Free Radical Catalysed Additions to the Double Bond of Diketene: A Synthesis of Novel Oxetan-2-Ones," 1986, Chem Soc Perkin Trans 1, 2081-2090.
Arnold, L.D., et al., "Synthesis of Optically Pure α-Amino Acids via Salts of α-Amino-β-propiolactone," 1988, JACS, 110/7:2237-2241.
Brandao, F.B.B., et al., "Bioconversion of D,L-tert-leucine Nitrile to D-tert-leucine by Recombinant Cells Expressing Nitrile Hydratase and D-selective Amidase," 2004, Eng Life Sci, 4/6:547-556.
Buchardt, J., et al., "Novel Methodology for the Solid-Phase Synthesis of Phosphinic Peptides," 2000, JCS, Perkin Trans 1, 3306-3310.
Dale, J., et al., "Macrocyclic Oligolactones by Oligomerization of Simple Lactones," 1986, Acta Chemica Scandinavica B, 40:559-567.
Groger, H., et al., "Chapter 8. Methods for the Enantioselective Biocatalytic Production of L-Amino Acids on the Industrial Scale," 2004, Asymmetric Catalysis on Industrial Scale, Blaser and Schmidt, E.Eds, Wiley, 143-145.
Gunnlaugsson, T., et al., "Fluorescent Photoinduced Electron Transfer (PET) Sensing of Anions Using Charge Nuetral Chemosensors," 2001, Chem Commun, 2556-2557.
Hensel, M., et al., "Stereoselective Hydration of R,S-phenylglycine Nitrile by New Whole Cell Biocatalysts," 2002, Tetrahedron: Asymmetry, 13:2629-2633.
Luknitskii, F.I., et al., "Synthesis and Reactions of pβ-Lactone and β-Sultone wth a Trichloromethyl Group in the β-Position," 1967, ZH ORG KHIM, 3/8:1456-1458.
Nakahara, T., et al., "Production of 2-Ketobutyric Acid from 1,2-Butanediol by Resting Cells of Rhodococcus Equi IFO 3730," 1994, Biotechnology Letters, 16/3:263-268.
Perchyonok, V.T., et al., "Recent Advances in Free Radical Chemistry of C—C Bond Formation in Aqueous Media: From Mechanistic Origins to Applications," 2008, Mini-Reviews, Org Chem, 5:19-32.
Rajadell, F., et al., "Competition between Decarboxylation and Isomerization in the C3H5O2 Energy Surface. Justification of the Experimental Results by Molecular Orbital Calculations on the Solvated Ions," 1994, J Phys Org Chem, 7:221-226.
Shigeno, T., et al., "Production of Pyruvic Acid from 1,2-Propanediol by *Pseudomonas* sp. Strain TB-135 Which does not Require Thiamine," 1991, Biotechnol Letters, 13/11:821-826.
Wang, M.X., "Practical and Convenient Enzymatic Synthesis of Enantiopure α-Amino Acids and Amides," 2002, J Org Chem, 67:6542-6545.
Antoniotti, S., et al., "Studies on the Catalytic Oxidation of Epoxides to α-Diketones by Bi(0)/O2 in DMSO," 2004, J Molecular Catalysis A: Chemical, 208:135-145.
Liu, X., et al., "Enantioselective Synthesis of Phosphinyl Peptidomimetics via an Asymmetric Michael Reaction of Phosphinic Acids with Acrylate Derivatives," 2002, J Organometallic Chem, 646:212-222.
Zeiss, H.J., Enantioselective Synthesis of Both Enantiomers of Phosphinothricin via Asymmetric Hydrogenation of α-Acylamido Acrylates, 1991, J Org Chem, 56:1783-1788, 6 pages.

SEQUENCE LISTING

```
<160> NUMBER OF SEQ ID NOS: 8

<210> SEQ ID NO 1
<211> LENGTH: 1101
<212> TYPE: DNA
<213> ORGANISM: Artificial Sequence
<220> FEATURE:
<223> OTHER INFORMATION: Synthetic Construct

<400> SEQUENCE: 1
atggttgaat acaccaacac cttcaaagtt gctgcagtac aggctcagcc ggtttggttt      60
gatgctgcta agaccgttga caaaactgta tctatcatcg ctgaagctgc tcgtaacggt     120
tgcgaactgg ttgctttccc ggaagttttc atcccgggtt acccgtacca catctgggtt     180
gactctccgc tggcaggtat ggctaaattc gcagtacgct accatgagaa ctctctgact     240
atggacagcc cgcacgtaca gcgtctgctg gatgcagctc gtgaccacaa tatcgcagta     300
gttgtaggta tttctgagcg cgacggtggc agcctgtaca tgacccagct ggtgatcgat     360
gcggatggtc agctggtggc ccgtcgtcgt aaactgaagc cgacccacgt agaacgttcc     420
gtatacggtg agggtaacgg cagcgacatc tctgtttatg acatgccgtt cgcccgtctg     480
ggcgcactga attgctggga acatttccag accctgacca aatacgctat gtactctatg     540
cacgagcagg tgcatgtggc ctcttggccg ggcatgtccc tgtaccagcc ggaggttcct     600
gctttcggtg ttgatgcgca gctgaccgcg actcgcatgt acgctctgga aggtcaaacc     660
tttgtcgtat gtaccacgca ggtcgtaacc ccggaagccc atgagttctt ctgcgacaac     720
gacgaacagc gtaaactgat cggccgtggt ggtgatttcg cgcgtattat cggcccggat     780
ggccgtgacc tggcgactcc actggcagag gacgaagaag gcatcctgta cgctgatatc     840
gacctgtctg ccatcactct ggcgaaacag gccgcggacc cggttggcca ttacagccgt     900
ccggacgtac tgtccctgaa ctttaatcag cgtcacacta ccccggttaa cactgctatt     960
tctacgatcc acgcaactca tactctggtt ccgcagtctg gcgcgctgga cggcgtccgt    1020
gaactgaacg gtgcagacga gcagcgtgcg ctgccgtcta cccactctga tgaaaccgat    1080
cgtgctactg cctctatcta a                                              1101

<210> SEQ ID NO 2
<211> LENGTH: 1075
<212> TYPE: DNA
<213> ORGANISM: Artificial Sequence
<220> FEATURE:
```

<223> OTHER INFORMATION: Sythetic Construct

<400> SEQUENCE: 2

| | |
|---|---|
| atgggtctga ctcgtaaaat cgtacgtgct gcagcagtac aggctgcttc tccgaactat | 60 |
| gatctggcaa ctggcgtaga caaaaccatc gaactggctc gtcaggctcg tgatgaaggc | 120 |
| tgtgatctga tcgttttcgg tgagacttgg ctgccgggtt acccgtttca cgtatggctg | 180 |
| ggcgctccgg cttggtccct gaaatactct gctcgttact acgctaactc tctgtctctg | 240 |
| gactctgctg aatttcagcg tatcgcacag gctgctcgta ctctgggtat cttcatcgct | 300 |
| ctgggttact ctgaacgctc tggtggttct ctgtacctgg tcagtgcct gatcgacgac | 360 |
| aaaggtcaga tgctgtggtc tcgtcgcaaa ctgaaaccga ctcacgttga acgtactgta | 420 |
| ttcggcgaag ttacgctcg tgatctgatc gtttctgata ctgaactggg tcgtgttggc | 480 |
| gcactgtgct gttgggagca cctgtctccg ctgtctaaat acgctctgta ttctcagcac | 540 |
| gaagctatcc acatcgctgc ttggccgtct ttctctctgt actctgaaca ggctcacgct | 600 |
| ctgtctgcta aagttaacat ggctgcatct cagatctact ccgttgaagg tcagtgcttc | 660 |
| actatcgctg catcttctgt tgttacccag gaaactctgg acatgctgga agttggtgaa | 720 |
| cacaacgcat ctctgctgaa agttggtggt ggctcctcta tgatctttgc tccggatggt | 780 |
| cgtactctgg ctccgtacct gccgcacgac gctgagggtc tgatcatcgc tgatctgaac | 840 |
| atggaagaaa tcgctttcgc taaagctatc aacgacccgg taggtcacta ctctaagccg | 900 |
| gaagcaaccc gtctggtact ggatctgggc caccgtgaac cgatgactcg tgtacactct | 960 |
| aaatctgtta tccaggaaga agctccggaa ccgcacgttc agtctaccgc tgcaccggtt | 1020 |
| gcagtttctc agactcagga ctctgacacc ctgctggttc aggaaccgtc ttaat | 1075 |

<210> SEQ ID NO 3
<211> LENGTH: 1041
<212> TYPE: DNA
<213> ORGANISM: Artificial Sequence
<220> FEATURE:
<223> OTHER INFORMATION: Synthetic Construct

<400> SEQUENCE: 3

| | |
|---|---|
| atgtcctcta ccaaagacat gtctactgta cagaacgcta ccccgtttaa cggtgttgct | 60 |
| ccgtctacta ccgtacgtgt tactattgtt cagtcttcta ctgtatacaa cgataccccg | 120 |
| gcgaccatcg acaaggcaga aaaatacatc gtagaggctg catctaaagg tgctgaactg | 180 |
| gttctgtttc cggaaggttt cattggcggt tacccacgtg gcttccgctt cggcctggcc | 240 |
| gttggtgtac acaacgaaga aggtcgcgat gaatttcgta aatatcatgc aagcgctatc | 300 |
| cacgttccgg gccagaggt agcgcgcctg ccgacgttg cacgcaaaaa ccatgtatac | 360 |
| ctggtgatgg gtgcgattga aaaagagggt acaccctgt attgcaccgt cctgttcttc | 420 |
| tccccacagg gtcagtttct gggtaagcac cgcaaactga tgccgacttc cctgaacgt | 480 |
| tgcatctggg gtcagggtga cggctctacc atccctgttt atgacactcc gattggcaaa | 540 |
| ctgggtgcag cgatttgctg ggaaaaccgc atgccgctgt atcgtaccgc tctgtacgct | 600 |
| aaaggtatcg aactgtattg tgctccgacc gctgacggct ctaaagaatg gcagtcttct | 660 |
| atgctgcaca tcgctattga aggtggttgt ttcgttctgt ctgcttgtca gttttgtcag | 720 |
| cgtaagcact ccccggatca cccggactac ctgttcactg attggtatga cgataaggag | 780 |
| cacgactcta tcgtttctca gggcggtctc ttatcatct ctccgctggg tcaggtactg | 840 |
| gctggtccga actttgaatc tgaaggcctg gttaccgctg acattgacct gggtgatatc | 900 |

| | |
|---|---|
| gcacgtgcta aactgtactt cgactctgtt ggtcactact ctcgtccgga tgttctgcac | 960 |
| ctgactgtta acgaacatcc gcgtaaatct gttacctttg taactaaagt tgaaaaagca | 1020 |
| gaggacgact ctaacaaata a | 1041 |

<210> SEQ ID NO 4
<211> LENGTH: 1074
<212> TYPE: DNA
<213> ORGANISM: Artificial Sequence
<220> FEATURE:
<223> OTHER INFORMATION: Synthetic Construct

<400> SEQUENCE: 4

| | |
|---|---|
| atgtccaccc atcaacagga tatgtctctg gtaacttcta ctccaccgat taacaacggc | 60 |
| aaccaaatct tcccggagat tgaaatgtcc ggtgatagca gctccatcgt acgcgccact | 120 |
| gtggtccagg cttgcactat tttctacgac actccggcta cgctggataa agcggagcgc | 180 |
| ctgctggctg aagctgccga taacggctct cagctggttg tattcccgga agcattcatc | 240 |
| ggcggctacc cgcgtggctc ttctttcgaa ctggcgatcg gcgcacgtac cgcaaagggt | 300 |
| cgtgatgatt ccgcaaaata tctggcttct gccattgacg tcccaggccc ggaagttgaa | 360 |
| cgtatggctg aaatggcgcg taaatacaag gtgttcctgg ttatgggcgt tattgaacgc | 420 |
| gaaggctata ccctgtactg ctctgttctg ttttcgact cccacggcca gttcctgggc | 480 |
| aaacaccgta aactgatgcc gaccgcactg gaacgttgca tttgggctt tggcgatggt | 540 |
| tctacgattc cggtctttga caccccctatc ggtaaaatcg gtgccgcaat ctgttgggaa | 600 |
| aaccgcatgc cgagcctgcg taccgcgatg tatgctaaag gtattgaaat ctactgcgca | 660 |
| cctaccgcag atgcgcgcga aacctggctg gcgtccatga cccacatcgc gctggaaggt | 720 |
| ggttgcttcg tactgtccgc taaccagttc tgtcgccgta agattaccc accgccaccg | 780 |
| gaatacactt tctccggttc cgaagagagc ctgaccccag attctgtcgt atgtgctggt | 840 |
| ggcagctcta ttatctctcc gctgggtatt gttctggcag gtccgaacta cgaaggtgaa | 900 |
| ggcctgatta gcgcagatct ggacctgggc gacattgcac gtgcgaaatt cgacttcgac | 960 |
| gtggtgggcc attattcccg tccggaggtt ttctctctga acatcaaaga gcaccgcgt | 1020 |
| aaggcagttt ccttcacttc taaagtaacc aaagatgaaa ccgtaaagaa ctaa | 1074 |

<210> SEQ ID NO 5
<211> LENGTH: 1053
<212> TYPE: DNA
<213> ORGANISM: Artificial Sequence
<220> FEATURE:
<223> OTHER INFORMATION: Synthetic Construct

<400> SEQUENCE: 5

| | |
|---|---|
| atgagcggct ccgaagaaat gtctaaagca ctgaacgcaa cgactccagg cttcccggac | 60 |
| atcccgtcca ctatcgtacg cgcgacgatc gtgcaggcct ctaccgtcta caacgacact | 120 |
| ccgaagacta tcgaaaaagc ggaaaaattc atcgcggagg ccgcatccga cggcgctcaa | 180 |
| ctggtggtgt cccggaggc gttcattgct ggctatccgc gtggctaccg tttcggtatt | 240 |
| ggtgttggcg tgcacaacga ggctggccgt gactgttttcc gtcgttacca tgctagcgca | 300 |
| atcgtggtgc cgggtccgga ggttgataaa ctggcagaaa tcgctcgcaa atacaaagtc | 360 |
| tatctggtta tgggtgctat ggaaaaagac ggttatacgc tgtactgcac cgctctgttc | 420 |
| ttctccagtg aaggtcgttt tctgggtaaa caccgtaagg ttatgccaac ttctctggaa | 480 |

```
cgttgcatct ggggtttcgg tgatggttcc actattccgg tttatgatac cccgctgggt      540
aaactgggtg cggccatctg ctgggaaaat cgtatgccgc tgtatcgtac cagcctgtac      600
ggtaaaggta ttgaactgta ctgcgctcct accgccgacg gcagcaaaga atggcagagc      660
tctatgatgc atatcgcgat cgaaggtggt tgtttcgtac tgtccgcttg tcagttttgc      720
ctgcgtaaag acttcccgga ccacgcggat tatctgttta ctgactggta ccctgaccag      780
caccaggaag cgatcgtatc tcaggtggt tctgttatca ttagcccact gggcaaaatc       840
ctggcaggtc cgaatttcga gagcgagggt ctgattaccg ctgacctgga cctgggcgac      900
gtggctcgcg cgaaactgta cttcgatgtt gtgggtcact actcccgccc tgaaatcttt      960
aatctgaccg tgaacgagac tccgaagaaa ccggtaacct tcgtaagcaa aagcgtgaaa     1020
gcggaagacg actccgaacc gcaggacaaa taa                                  1053
```

<210> SEQ ID NO 6
<211> LENGTH: 1050
<212> TYPE: DNA
<213> ORGANISM: Artificial Sequence
<220> FEATURE:
<223> OTHER INFORMATION: Synthetic Construct

<400> SEQUENCE: 6

```
atgaccgtcc ataaaaagca gtataaagtg gcggcagttc aggctgcacc ggccttcctg       60
gacctggaag ctggtgtggc aaaagcgatc ggtctgatcg cgcaggcggc tgcggaaggt      120
gcgtccctgg tggcgttccc ggaggcttgg ctgccgggct accgtggtg gatctggctg      180 gattctccgg caggcggtat gcgctttgta cagcgtaact tcgacaacgc cctggaagtt      240
ggcagcgaac cattcgagcg tctgtgccgt gcagcagcac agcataaaat ctacgtcgtt      300
ctgggtttta cggaacgttc tggcggtact ctgtatctgg cacaggcgat cattgacgac      360
tgtggccgtg tggtcgcgac tcgtcgtaaa ctgaagccaa ctcacgtaga acgctccgta      420
tacggcgaag cgacggttc cgatctggct gttcatgaca ctacccctggg tcgtctgggc      480 gcgctgtgct gcgcagaaca tatccagccg ctgagcaaat acgctatgta cgcacagcac      540
gagcaggtgc atatcgcggc gtggccgagc ttttctgtgt atcgtggcgc tgcatttcag      600
ctgtctgcgc aggctaacaa cgcggcttcc caagtttatg cgctggaggg tcagtgcttc      660
gttctggcac catgtgcccc ggtgagcaaa gaaatgctgg atgaactgat tgattctccg      720
gctaaagctg aactgctgct ggagggcggt ggcttcgcca tgatctacgg tccggatggt      780
gctccgctgt gcaccccgct ggcggaaacc gaagaaggta tcctgtacgc agacatcgat      840
ctgggcgtga tcggtgttgc gaaagcagct tacgacccgg ttggccacta ctcccgtccg      900
gacgtcctgc gtctgctggt taaccgtgaa ccgatgaccc gtgttcatta tgtacagccg      960
cagagcctgc cggaaacctc tgtactggcg ttcggcgcag gtgctgatgc tattcgtagc     1020
gaagaaaacc cggaagaaca gggtgataaa                                      1050
```

<210> SEQ ID NO 7
<211> LENGTH: 4978
<212> TYPE: DNA
<213> ORGANISM: Artificial Sequence
<220> FEATURE:
<223> OTHER INFORMATION: Synthetic Construct

<400> SEQUENCE: 7

```
ctcatgacca aaatccctta acgtgagtta cgcgcgcgtc gttccactga gcgtcagacc       60
ccgtagaaaa gatcaaagga tcttcttgag atcctttttt tctgcgcgta atctgctgct      120
```

```
tgcaaacaaa aaaaccaccg ctaccagcgg tggtttgttt gccggatcaa gagctaccaa      180 ctcttttttcc gaaggtaact ggcttcagca gagcgcagat accaaatact gttcttctag     240
tgtagccgta gttagcccac cacttcaaga actctgtagc accgcctaca tacctcgctc     300
tgctaatcct gttaccagtg gctgctgcca gtggcgataa gtcgtgtctt accgggttgg      360
actcaagacg atagttaccg gataaggcgc agcggtcggg ctgaacgggg ggttcgtgca     420
cacagcccag cttggagcga acgacctaca ccgaactgag atacctacag cgtgagctat     480
gagaaagcgc cacgcttccc gaagggagaa aggcggacag gtatccggta agcggcaggg     540
tcggaacagg agagcgcacg agggagcttc caggggggaaa cgcctggtat ctttatagtc    600
ctgtcgggtt tcgccacctc tgacttgagc gtcgattttt gtgatgctcg tcagggggggc   660 ggagcctatg gaaaaacgcc agcaacgcgg ccttttttacg gttcctggcc ttttgctggc   720
cttttgctca catgttcttt cctgcgttat ccctgattc tgtggataac cgtattaccg      780
cctttgagtg agctgatacc gctcgccgca gccgaacgac cgagcgcagc gagtcagtga     840
gcgaggaagc ggaaggcgag agtagggaac tgccaggcat caaactaagc agaaggcccc     900
tgacggatgg ccttttttgcg tttctacaaa ctctttctgt gttgtaaaac gacggccagt    960
cttaagctcg ggccccctgg gcggttctga taacgagtaa tcgttaatcc gcaaataacg    1020
taaaaacccg cttcggcggg ttttttttatg ggggagttt agggaaagag catttgtcag   1080
aatatttaag ggcgcctgtc actttgcttg atatatgaga attatttaac cttataaatg    1140
agaaaaaagc aacgcacttt aataagata cgttgctttt tcgattgatg aacacctata     1200
attaaactat tcatctatta tttatgattt tttgtatata caatatttct agtttgttaa    1260
agagaattaa gaaataaat ctcgaaaata ataagggaa aatcagtttt tgatatcaaa      1320
attatacatg tcaacgataa tacaaaatat aatacaaact ataagatgtt atcagtattt    1380
attatgcatt tagaataaat tttgtgtcgc ccttaattgt gagcggataa caattacgag    1440
cttcatgcac agtgaaatca tgaaaaattt atttgctttg tgagcggata acaattataa   1500
tatgtggaat tgtgagcgct cacaattcca caacggtttc cctctagaaa taattttgtt   1560 taactttttag gaggtaaaac atatgtcctc taccaaagac atgtctactg tacagaacgc   1620 tacccccgttt aacggtgttg ctccgtctac taccgtacgt gttactattg ttcagtcttc   1680
tactgtatac aacgataccc cggcgaccat cgacaaggca gaaaaataca tcgtagaggc   1740
tgcatctaaa ggtgctgaac tggttctgtt tccggaaggt ttcattggcg gttacccacg   1800
tggcttccgc ttcggcctgg ccgttggtgt acacaacgaa gaaggtcgcg atgaatttcg   1860
taaatatcat gcaagcgcta tccacgttcc gggcccagag gtagcgcgcc tggccgacgt   1920
tgcacgcaaa aaccatgtat acctggtgat gggtgcgatt gaaaaagagg gttacaccct   1980
gtattgcacc gtcctgttct tctccccaca gggtcagttt ctgggtaagc accgcaaact   2040
gatgccgact tccctggaac gttgcatctg ggtcagggt gacggctcta ccatccctgt    2100
ttatgacact ccgattggca aactgggtgc agcgatttgc tgggaaaacc gcatgccgct   2160
gtatcgtacc gctctgtacg ctaaaggtat cgaactgtat tgtgctccga ccgctgacgg   2220
ctctaaagaa tggcagtctt ctatgctgca catcgctatt gaaggtggtt gtttcgttct   2280
gtctgcttgt cagttttgtc agcgtaagca cttcccggat caccccggact acctgttcac   2340 tgattggtat gacgataagg agcacgactc tatcgtttct cagggcggct ctgttatcat   2400
ctctccgctg ggtcaggtac tggctggtcc gaactttgaa tctgaaggcc tggttaccgc   2460
```

```
tgacattgac ctgggtgata tcgcacgtgc taaactgtac ttcgactctg ttggtcacta    2520
ctctcgtccg gatgttctgc acctgactgt taacgaacat ccgcgtaaat ctgttacctt    2580
tgtaactaaa gttgaaaaag cagaggacga ctctaacaaa taataagctt ccccaagggc    2640 gacacccct aattagcccg ggcgaaaggc ccagtctttc gactgagcct ttcgttttat     2700
ttgatgcctg gcagttccct actctcgcat ggggagtccc cacactacca tcggcgctac    2760
ggcgtttcac ttctgagttc ggcatggggt caggtgggac caccgcgcta ctgccgccag    2820
gcaaacaagg ggtgttatga gccatattca ggtataaatg ggctcgcgat aatgttcaga    2880
attggttaat tggttgtaac actgacccct atttgtttat ttttctaaat acattcaaat    2940
atgtatccgc tcatgagaca ataaccctga taaatgcttc aataatattg aaaaaggaag    3000
aatatgagcc atattcaacg ggaaacgtcg aggccgcgat taaattccaa catggatgct    3060
gatttatatg ggtataaatg gctcgcgat aatgtcgggc aatcaggtgc gacaatctat     3120
cgcttgtatg ggaagcccga tgcgccagag ttgtttctga acatggcaa aggtagcgtt     3180 gccaatgatg ttacagatga gatggtcaga ctaaactggc tgacggaatt tatgccactt    3240
ccgaccatca agcattttat ccgtactcct gatgatgcat ggttactcac cactgcgatc    3300 cccgaaaaa cagcgttcca ggtattagaa gaatatcctg attcaggtga aaatattgtt     3360
gatgcgctgg cagtgttcct gcgccggttg cactcgattc ctgtttgtaa ttgtcctttt    3420
aacagcgatc gcgtatttcg cctcgctcag gcgcaatcac gaatgaataa cggtttggtt    3480
gatgcgagtg attttgatga cgagcgtaat ggctggcctg ttgaacaagt ctggaaagaa    3540
atgcataaac ttttgccatt ctcaccggat tcagtcgtca ctcatggtga tttctcactt    3600 gataaccta ttttttgacga ggggaaatta ataggttgta ttgatgttgg acgagtcgga    3660
atcgcagacc gataccagga tcttgccatc ctatggaact gcctcggtga gttttctcct    3720
tcattacaga aacggctttt tcaaaaatat ggtattgata atcctgatat gaataaattg    3780
cagtttcatt tgatgctcga tgagtttttc taagcggcgc gccatcgaat ggcgcaaaac    3840
ctttcgcggt atggcatgat agcgcccgga agagagtcaa ttcagggtgg tgaatatgaa    3900
accagtaacg ttatacgatg tcgcagagta tgccggtgtc tcttatcaga ccgtttcccg    3960
cgtggtgaac caggccagcc acgtttctgc gaaaacgcgg gaaaaagtgg aagcggcgat    4020
ggcggagctg aattacattc ccaaccgcgt ggcacaacaa ctggcgggca aacagtcgtt    4080
gctgattggc gttgccacct ccagtctggc cctgcacgcg ccgtcgcaaa ttgtcgcggc    4140
gattaaatct cgcgccgatc aactgggtgc cagcgtggtg gtgtcgatgg tagaacgaag    4200
cggcgtcgaa gcctgtaaag cggcggtgca caatcttctc gcgcaacgcg tcagtgggct    4260
gatcattaac tatccgctgg atgaccagga tgccattgct gtggaagctg cctgcactaa    4320
tgttccggcg ttatttcttg atgtctctga ccagacaccc atcaacagta ttattttctc    4380
ccatgaggac ggtacgcgac tgggcgtgga gcatctggtc gcattgggtc accagcaaat    4440
cgcgctgtta gcgggcccat taagttctgt ctcggcgcgt ctgcgtctgg ctggctggca    4500
taaatatctc actcgcaatc aaattcagcc gatagcggaa cgggaaggcg actggagtgc    4560
catgtccggt tttcaacaaa ccatgcaaat gctgaatgag gcatcgttc ccactgcgat     4620 gctggttgcc aacgatcaga tggcgctggg cgcaatgcgc gccattaccg agtccgggct    4680
gcgcgttggt gcggatatct cggtagtggg atacgacgat accgaagata gctcatgtta    4740
tatcccgccg ttaaccacca tcaaacagga ttttcgcctg ctggggcaaa ccagcgtgga    4800
ccgcttgctg caactctctc agggccaggc ggtgaagggc aatcagctgt tgccagtctc    4860
```

```
actggtgaaa agaaaaacca ccctggcgcc caatacgcaa accgcctctc cccgcgcgtt    4920
ggccgattca ttaatgcagc tggcacgaca ggtttcccga ctggaaagcg ggcagtga      4978
```

<210> SEQ ID NO 8
<211> LENGTH: 5038
<212> TYPE: DNA
<213> ORGANISM: Artificial Sequence
<220> FEATURE:
<223> OTHER INFORMATION: Synthetic Construct

<400> SEQUENCE: 8

```
ctcatgacca aaatccctta acgtgagtta cgcgcgcgtc gttccactga gcgtcagacc      60
ccgtagaaaa gatcaaagga tcttcttgag atccttttt  tctgcgcgta atctgctgct     120
tgcaaacaaa aaaaccaccg ctaccagcgg tggtttgttt gccggatcaa gagctaccaa     180
ctctttttcc gaaggtaact ggcttcagca gagcgcagat accaaatact gttcttctag     240
tgtagccgta gttagcccac cacttcaaga actctgtagc accgcctaca tacctcgctc     300
tgctaatcct gttaccagtg ctgctgccag tggcgataag tcgtgtcttt accgggttgg     360
actcaagacg atagttaccg gataaggcgc agcggtcggg ctgaacgggg gttcgtgca     420 cacagcccag cttggagcga acgacctaca ccgaactgag atacctacag cgtgagctat     480
gagaaagcgc cacgcttccc gaagggagaa aggcggacag gtatccggta agcggcaggg     540
tcggaacagg agagcgcacg agggagcttc caggggggaaa cgcctggtat ctttatagtc     600
ctgtcgggtt tcgccacctc tgacttgagc gtcgattttt gtgatgctcg tcaggggggc     660
ggagcctatg gaaaaacgcc agcaacgcgg ccttttttacg gttcctggcc ttttgctggc     720
cttttgctca catgttcttt cctgcgttat cccctgattc tgtggataac cgtattaccg     780
cctttgagtg agctgatacc gctcgccgca gccgaacgac cgagcgcagc gagtcagtga     840
gcgaggaagc ggaaggcgag agtagggaac tgccaggcat caaactaagc agaaggcccc     900
tgacggatgg cctttttgcg tttctacaaa ctctttctgt gttgtaaaac gacggccagt     960
cttaagctcg ggcccctgg  gcggttctga taacgagtaa tcgttaatcc gcaaataacg    1020
taaaaacccg cttcggcggg ttttttatg  ggggagttt  agggaaagag catttgtcag    1080
aatatttaag ggcgcctgtc actttgcttg atatatgaga attatttaac cttataaatg    1140
agaaaaaagc aacgcacttt aaataagata cgttgctttt tcgattgatg aacacctata    1200
attaaactat tcatctatta tttatgattt tttgtatata caatatttct agtttgttaa    1260
agagaattaa gaaaataaat ctcgaaaata ataagggaa  aatcagtttt tgatatcaaa    1320
attatacatg tcaacgataa tacaaaatat aatacaaact ataagatgtt atcagtattt    1380
attatgcatt tagaataaat tttgtgtcgc ccttaattgt gagcggataa caattacgag    1440
cttcatgcac agtgaaatca tgaaaaattt atttgctttg tgagcggata acaattataa    1500
tatgtggaat tgtgagcgct cacaattcca caacggtttc cctctagaaa taattttgtt    1560 taactttag  gaggtaaaac atatggttga atacaccaac accttcaaag ttgctgcagt    1620
acaggctcag ccggttttggt ttgatgctgc taagaccgtt gacaaaactg tatctatcat    1680
cgctgaagct gctcgtaacg gttgcgaact ggttgctttc ccggaagttt tcatcccggg    1740
ttacccgtac cacatctggg ttgactctcc gctggcaggt atggctaaat cgcagtacg     1800 ctaccatgag aactctctga ctatggacag cccgcacgta cagcgtctgc tggatgcagc    1860
tcgtgaccac aatatcgcag tagttgtagg tatttctgag cgcgacggtg gcagcctgta    1920
```

-continued

```
catgacccag ctggtgatcg atgcggatgg tcagctggtg gcccgtcgtc gtaaactgaa    1980
gccgacccac gtagaacgtt ccgtatacgg tgagggtaac ggcagcgaca tctctgttta    2040
tgacatgccg ttcgcccgtc tgggcgcact gaattgctgg gaacatttcc agaccctgac    2100
caaatacgct atgtactcta tgcacgagca ggtgcatgtg gcctcttggc cgggcatgtc    2160
cctgtaccag ccggaggttc ctgctttcgg tgttgatgcg cagctgaccg cgactcgcat    2220
gtacgctctg gaaggtcaaa cctttgtcgt atgtaccacg caggtcgtaa ccccggaagc    2280
ccatgagttc ttctgcgaca acgacgaaca gcgtaaactg atcggccgtg gtggtggttt    2340
cgcgcgtatt atcggcccgg atggccgtga cctggcgact ccactggcag aggacgaaga    2400
aggcatcctg tacgctgata tcgacctgtc tgccatcact ctggcgaaac aggccgcgga    2460
cccggttggc cattacagcc gtccggacgt actgtccctg aactttaatc agcgtcacac    2520
taccccggtt aacactgcta tttctacgat ccacgcaact catactctgg ttccgcagtc    2580
tggcgcgctg gacggcgtcc gtgaactgaa cggtgcagac gagcagcgtg cgctgccgtc    2640
tacccactct gatgaaaccg atcgtgctac tgcctctatc taataagctt ccccaagggc    2700
gacaccccct aattagcccg ggcgaaaggc ccagtctttc gactgagcct ttcgttttat    2760
ttgatgcctg gcagttccct actctcgcat ggggagtccc cacactacca tcggcgctac    2820
ggcgtttcac ttctgagttc ggcatggggt caggtgggac caccgcgcta ctgccgccag    2880
gcaaacaagg ggtgttatga gccatattca ggtataaatg ggctcgcgat aatgttcaga    2940
attggttaat tggttgtaac actgacccct atttgtttat ttttctaaat acattcaaat    3000
atgtatccgc tcatgagaca ataaccctga taaatgcttc aataatattg aaaaaggaag    3060
aatatgagcc atattcaacg ggaaacgtcg aggccgcgat taaattccaa catggatgct    3120
gatttatatg ggtataaatg ggctcgcgat aatgtcgggc aatcaggtgc gacaatctat    3180
cgcttgtatg ggaagcccga tgcgccagag ttgtttctga acatggcaa aggtagcgtt    3240
gccaatgatg ttacagatga gatggtcaga ctaaactggc tgacggaatt tatgccactt    3300
ccgaccatca agcattttat ccgtactcct gatgatgcat ggttactcac cactgcgatc    3360
cccgaaaaaa cagcgttcca ggtattagaa gaatatcctg attcaggtga aaatattgtt    3420
gatgcgctgg cagtgttcct gcgccggttg cactcgattc ctgtttgtaa ttgtcctttt    3480
aacagcgatc gcgtatttcg cctcgctcag gcgcaatcac gaatgaataa cggtttggtt    3540
gatgcgagtg attttgatga cgagcgtaat ggctggcctg ttgaacaagt ctggaaagaa    3600
atgcataaac ttttgccatt ctcaccggat tcagtcgtca ctcatggtga tttctcactt    3660
gataacctta ttttttgacga ggggaaatta ataggttgta ttgatgttgg acgagtcgga    3720
atcgcagacc gataccagga tcttgccatc ctatggaact gcctcggtga gttttctcct    3780
tcattacaga aacggctttt tcaaaaatat ggtattgata atcctgatat gaataaattg    3840
cagtttcatt tgatgctcga tgagtttttc taagcggcgc gccatcgaat ggcgcaaaac    3900
ctttcgcggt atggcatgat agcgcccgga agagagtcaa ttcagggtgg tgaatatgaa    3960
accagtaacg ttatacgatg tcgcagagta tgccggtgtc tcttatcaga ccgtttcccg    4020
cgtggtgaac caggccagcc acgtttctgc gaaaacgcgg gaaaagtgg aagcggcgat    4080
ggcggagctg aattacattc ccaaccgcgt ggcacaacaa ctggcgggca acagtcgtt    4140
gctgattggc gttgccacct ccagtctggc cctgcacgcg ccgtcgcaaa ttgtcgcggc    4200
gattaaatct cgcgccgatc aactgggtgc cagcgtggtg gtgtcgatgg tagaacgaag    4260
cggcgtcgaa gcctgtaaag cggcggtgca caatcttctc gcgcaacgcg tcagtgggct    4320
```

```
gatcattaac tatccgctgg atgaccagga tgccattgct gtggaagctg cctgcactaa    4380
tgttccggcg ttatttcttg atgtctctga ccagacaccc atcaacagta ttattttctc    4440
ccatgaggac ggtacgcgac tgggcgtgga gcatctggtc gcattgggtc accagcaaat    4500
cgcgctgtta gcgggcccat taagttctgt ctcggcgcgt ctgcgtctgg ctggctggca    4560
taaatatctc actcgcaatc aaattcagcc gatagcggaa cgggaaggcg actggagtgc    4620
catgtccggt tttcaacaaa ccatgcaaat gctgaatgag ggcatcgttc ccactgcgat    4680
gctggttgcc aacgatcaga tggcgctggg cgcaatgcgc gccattaccg agtccgggct    4740
gcgcgttggt gcggatatct cggtagtggg atacgacgat accgaagata gctcatgtta    4800
tatcccgccg ttaaccacca tcaaacagga ttttcgcctg ctggggcaaa ccagcgtgga    4860
ccgcttgctg caactctctc agggccaggc ggtgaagggc aatcagctgt tgccagtctc    4920
actggtgaaa agaaaaacca ccctggcgcc caatacgcaa accgcctctc cccgcgcgtt    4980
ggccgattca ttaatgcagc tggcacgaca ggtttcccga ctggaaagcg ggcagtga     5038
```

PROCESS OF PRODUCING PHOSPHINOTHRICIN EMPLOYING NITRILASES

REFERENCE TO CORRESPONDING APPLICATIONS

This application is a divisional of U.S. patent application Ser. No. 13/640,833, filed Apr. 10, 2013, now U.S. Pat. No. 8,981,142, which is the 371 national stage of International PCT Application No. PCT/US2010/031007, filed Apr. 14, 2010.

FIELD OF THE INVENTION

The present invention generally relates to processes for the enzymatic production of a phosphinothricin product or precursor thereof from a nitrile-containing substrate.

BACKGROUND OF THE INVENTION

D,L-phosphinothricin (commonly referred to as glufosinate) and its salts and esters are known to be useful as a broad spectrum, non-selective herbicide. The ammonium salt of phosphinothricin is the most common commercially available form. The herbicidal efficacy of L-phosphinothricin or salts and esters thereof is generally about twice that of other stereoisomers, thereby generally requiring a reduced proportion of herbicide to provide the desired effect. Thus, the use of the L-stereoisomer is economically and ecologically advantageous.

Various multistep processes to prepare phosphinothricin are known in the art. For example, some routes utilize phosphorus trichloride to produce a phosphinate precursor, which is subjected to hydroformylation-aminocarbonylation, followed by hydrolysis to produce phosphinothricin. In particular, one process for producing phosphinothricin generally comprises converting phosphorus trichloride to methylphosphonous dichloride or a derivative thereof. The methylphosphonous dichloride or derivative thereof is then reacted with methanol to form methyl methylphosphinate. Methyl methylphosphinate is then reacted with vinylic compounds (e.g., vinyl acetate) to form an intermediate (e.g., 2-(methoxy(methyl)phosphoryl)ethyl acetate). The resulting intermediate is pyrolyzed to prepare a vinylphosphinate precursor. The vinylphosphinate precursor is subjected to hydroformylation-aminocarbonylation, followed by hydrolysis of the hydroformylation-aminocarbonylation product in the presence of hydrochloric acid to produce phosphinothricin.

Another process of producing phosphinothricin generally comprises converting phosphorus trichloride to an adduct of methylphosphonous trichloride and aluminum tetrachloride (i.e., $CH_3PCl_3 \cdot AlCl_4$). The adduct is reacted with ethylene to form an intermediate adduct, which is then reacted with ethanol to form ethyl 1-(2-chloroethyl)-methylphosphinate. This compound is reacted with potassium hydroxide and ethanol to prepare an ethyl vinylphosphinate precursor. The ethyl vinylphosphinate precursor is subjected to hydroformylation-aminocarbonylation, followed by hydrolysis of the hydroformylation-aminocarbonylation product in the presence of hydrochloric acid to produce phosphinothricin.

Other processes for producing phosphinothricin are described in, for example, U.S. Pat. Nos. 4,521,348; 6,335,186; and 6,359,162.

Although processes for the preparation of phosphinothricin are known in the art, there exists a need for a process that represents an improvement in process economics by virtue of requiring fewer process steps and fewer reagents than conventional processes. There also exists a need for an economical stereoselective process that preferentially produces L-phosphinothricin products or precursors thereof.

SUMMARY OF THE INVENTION

Briefly, therefore, the present invention is directed to processes for the enzymatic production of a phosphinothricin product or precursor thereof from a nitrile-containing substrate.

In one aspect, the present invention is directed to processes for the production of a phosphinothricin product or precursor thereof comprising contacting in a reaction mixture a nitrile-containing substrate with an enzyme capable of catalyzing the hydrolysis of —CN to —COX, wherein X is —OH or —$NH_2$. In another aspect, the present invention is directed to processes believed to be stereoselective for the production of L-phosphinothricin products or precursors thereof.

In various embodiments, the present invention is directed to processes for the preparation of a phosphinothricin product or precursor thereof. In one embodiment, the process comprises contacting in a reaction mixture a nitrile-containing substrate of Formula I

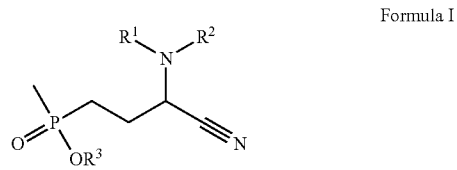

Formula I with an enzyme capable of catalyzing the hydrolysis of —CN to —COX, wherein X is either —OH or —$NH_2$; and wherein $R^1$ is hydrogen, —C(O)$R^4$, or substituted or unsubstituted $C_1$-$C_8$ alkyl;

$R^2$ is hydrogen, —C(O)$R^4$, —C(O)$R^5$, or substituted or unsubstituted $C_1$-$C_8$ alkyl; or $R^1$ and $R^2$ are part of a heterocyclic ring;

$R^3$ is hydrogen, substituted or unsubstituted $C_1$-$C_8$ alkyl, substituted or unsubstituted aryl, or an agronomically acceptable salt-forming cation; and $R^4$ and $R^5$ are independently hydrogen, substituted or unsubstituted $C_1$-$C_8$ alkyl, substituted or unsubstituted $C_1$-$C_8$ alkoxy, substituted or unsubstituted aryl, or substituted or unsubstituted furanyl.

In another embodiment, the process comprises:

(a) reacting acrolein with a compound of Formula II,

Formula II thereby forming a compound of Formula III;

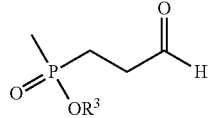
Formula III (b) reacting the compound of Formula III with a cyanide source and an ammonia source, thereby forming a nitrile-containing substrate of Formula IV,

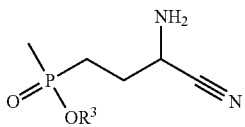
Formula IV wherein $R^3$ is hydrogen, substituted or unsubstituted $C_1$-$C_8$ alkyl, substituted or unsubstituted aryl, or an agronomically acceptable salt-forming cation; and (c) contacting in a reaction mixture the nitrile-containing substrate of Formula IV with an enzyme capable of catalyzing the hydrolysis of a —CN to —COX, wherein X is either —OH or —$NH_2$, thereby forming a phosphinothricin product or precursor thereof.

Yet another aspect of the present invention is directed to processes for the preparation of N-formyl substrates, which are useful in the production of phosphinothricin products or precursors thereof.

In one embodiment, the process comprises:

(a) reacting a compound of Formula III,

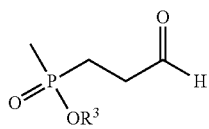
Formula III with a cyanide source and an ammonia source, thereby forming a nitrile-containing substrate of Formula IV,

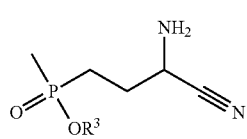
Formula IV (b) reacting the nitrile-containing substrate of Formula IV with one or more formylation reagents, thereby producing an N-formyl substrate of Formula V,

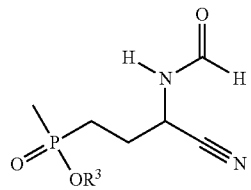
Formula V (c) contacting in a reaction mixture the N-formyl substrate of Formula V with an enzyme capable of catalyzing the hydrolysis of —CN to —COX, wherein X is either —OH or —NH; thereby producing a compound of Formula VII

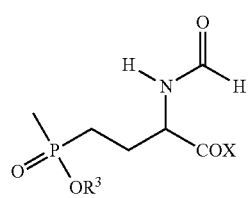
Formula VII wherein $R^3$ is hydrogen, substituted or unsubstituted ($C_1$-$C_8$) alkyl, substituted or unsubstituted aryl, or an agronomically acceptable salt-forming cation; and (d) hydrolyzing the compound of Formula VII to form a phosphinothricin product or precursor thereof.

The present invention is further directed to nitrile-containing compounds of Formula V

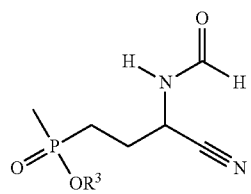
Formula V wherein $R^3$ is hydrogen, substituted or unsubstituted $C_1$-$C_8$ alkyl, substituted or unsubstituted aryl, or an agronomically acceptable salt-forming cation.

The present invention is still further directed to compounds having the structure of Formula VII

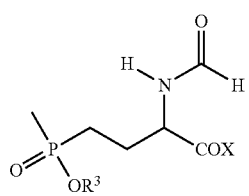
Formula VII wherein X is either —OH or —$NH_2$ and $R^3$ is hydrogen, substituted or unsubstituted ($C_1$-$C_8$) alkyl, substituted or unsubstituted aryl, or an agronomically acceptable salt-forming cation.

Another aspect of the present invention is directed to novel enzymes capable of catalyzing the hydrolysis of —CN to —COX, wherein X is —OH or —NH$_2$ and novel gene sequences that encode a nitrilase, which are useful in the enzymatic production of a phosphinothricin product or precursor thereof.

Other objects and features will be in part apparent and in part pointed out hereinafter.

INCORPORATION OF SEQUENCE LISTING

Figure 1:
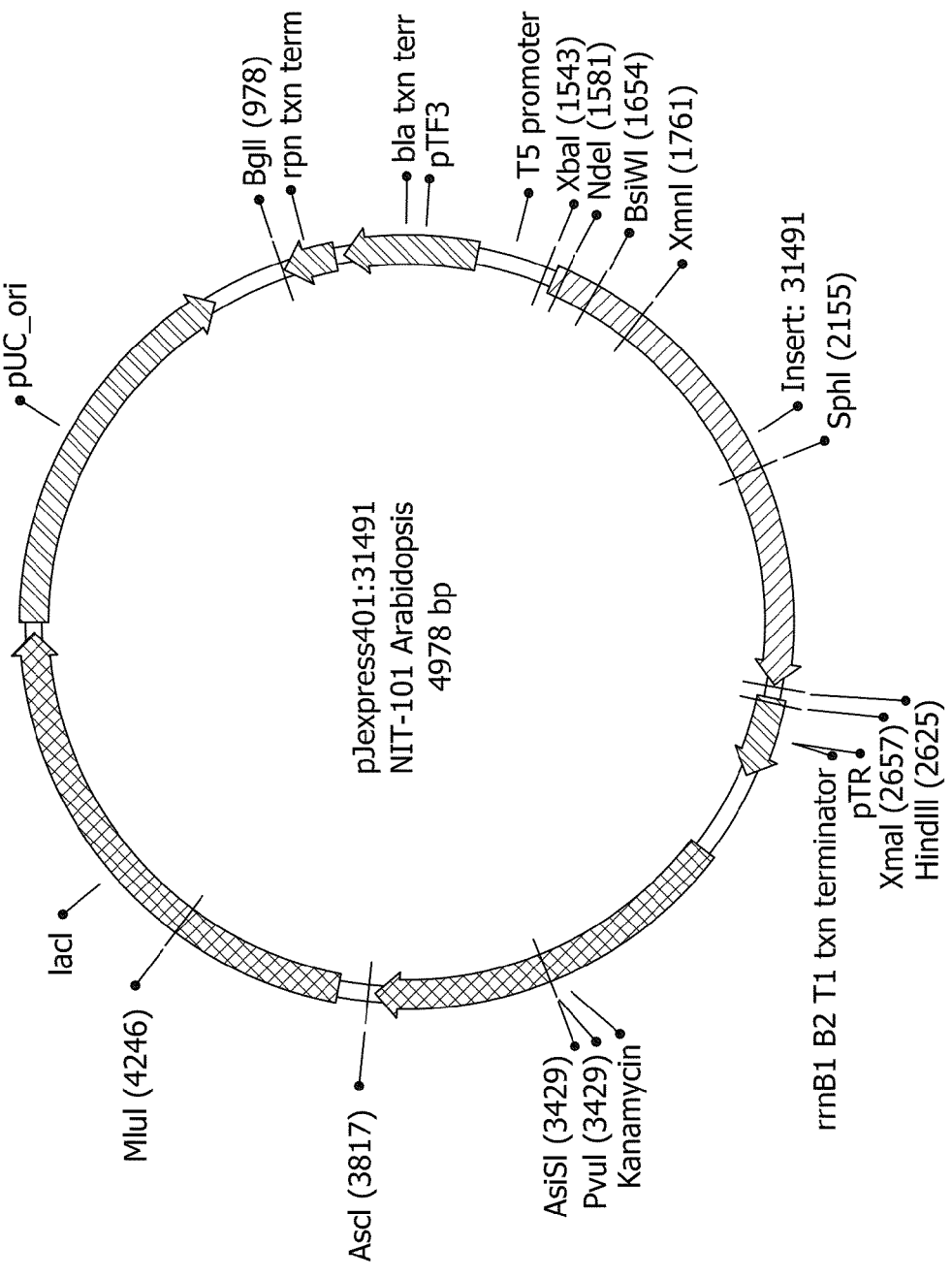
FIG. 1 is plasmid map pJexpress401:31491.

A sequence listing created using PatentIn Version 3.5 is being submitted herewith by electronic submission and is hereby incorporated herein by reference.

SEQ ID NO: 1 is a nucleotide sequence encoding a *R. rhodochrous* nitrilase.

SEQ ID NO: 2 is a nucleotide sequence encoding an *A. faecalis* nitrilase.

SEQ ID NO: 3 is a nucleotide sequence encoding an *A. thaliana* nitrilase.

SEQ ID NO: 4 is a nucleotide sequence encoding a *B. campestris* nitrilase.

SEQ ID NO: 5 is a nucleotide sequence encoding a *B. campestris* nitrilase.

SEQ ID NO: 6 is a nucleotide sequence encoding a *P. fluorescens* nitrilase.

SEQ ID NO: 7 is a nucleotide sequence for a plasmid pSEA99.

SEQ ID NO: 8 is a nucleotide sequence for a plasmid pSEA100.

DETAILED DESCRIPTION OF THE PREFERRED EMBODIMENTS

Described herein are processes for the enzymatic production of a phosphinothricin product or a precursor thereof (e.g., a compound of Formula VI described elsewhere herein). Processes of the present invention generally comprise contacting a nitrile-containing substrate (e.g., a compound of Formula I detailed elsewhere herein) with an enzyme capable of catalyzing the hydrolysis of a nitrile group (e.g., a nitrilase or a nitrile hydratase). Further described herein are processes for the preparation of N-formyl substrates suitable for use in the preparation of a phosphinothricin product or precursor thereof. Advantageously, the enzymatic processes of the present invention require reduced processing and/or reduced raw materials as compared to conventional processes.

Also described herein are processes for the preparation of phosphinothricin products or precursors thereof that are believed to be stereoselective and preferentially produce L-phosphinothricin products or precursors. L-phosphinothricin products are known to exhibit greater herbicidal efficacy than other phosphinothricin stereoisomers. Thus, processes of the present invention are believed to provide greater yields of herbicidally active compounds over conventional processes.

Moreover, described herein are novel compounds useful as intermediates in the preparation of a phosphinothricin product or precursor thereof. Also described herein are novel phosphinothricin precursors useful for the preparation of a phosphinothricin product (e.g. the acid of phosphinothricin).

Further described herein are novel enzymes and novel gene sequences that encode nitrilases, which are useful in the preparation of a phosphinothricin product or precursor thereof.

I. Substrates

In various embodiments, the present invention is directed to processes for preparing a phosphinothricin product or precursor thereof that comprise contacting in a reaction mixture a nitrile-containing substrate with an enzyme capable of catalyzing the hydrolysis of —CN to —COX, wherein X is —OH or —NH$_2$.

Suitable nitrile-containing substrates include substrates of Formula I:

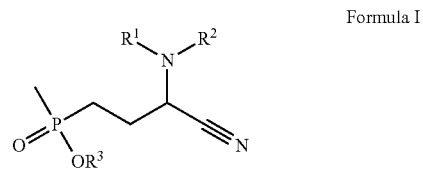

Formula I wherein
(i) $R^1$ is hydrogen, —C(O)R$^4$, or substituted or unsubstituted C$_1$-C$_8$ alkyl;
(ii) $R^2$ is hydrogen, —C(O)R$^4$, —C(O)R$^5$, or substituted or unsubstituted C$_1$-C$_8$ alkyl; or $R^1$ and $R^2$ are part of a heterocyclic ring;
(iii) $R^3$ is hydrogen, substituted or unsubstituted C$_1$-C$_8$ alkyl, substituted or unsubstituted aryl, or an agronomically acceptable salt-forming cation; and
(iv) $R^4$ and $R^5$ are independently hydrogen, substituted or unsubstituted C$_1$-C$_8$ alkyl, substituted or unsubstituted C$_1$-C$_8$ alkoxy, substituted or unsubstituted aryl, or substituted or unsubstituted furanyl.

As used herein, an "agronomically acceptable salt-forming cation" is defined as a salt-forming cation that allows agriculturally and economically useful herbicidal activity of a phosphinothricin anion. Such a cation may be, for example, an alkaline or alkaline earth metal cation (e.g., a sodium or potassium ion), an ammonium ion, an alkylammonium ion, a dialkylammonium ion, or trialkylammonium ion, or other metal cation such as copper, zinc, nickel, manganese and iron. In various embodiments, the salt-forming cation is an ammonium cation.

Often $R^1$ and $R^2$ are each hydrogen. In various embodiments, $R^1$, $R^2$, $R^4$ and $R^5$ are independently hydrogen or substituted or unsubstituted C$_1$-C$_8$ alkyl and $R^3$ is hydrogen or substituted or unsubstituted C$_1$-C$_8$ alkyl.

In still further embodiments, $R^2$ is —C(O)R$^4$ and $R^4$ is hydrogen. In other embodiments, $R^2$ is —C(O)R$^4$ and $R^4$ is substituted or unsubstituted C$_1$-C$_8$ alkoxy and more preferably C$_1$ or C$_2$ alkoxy.

In various embodiments, $R^3$ is substituted or unsubstituted C$_1$-C$_8$ alkyl, substituted or unsubstituted aryl, or an agronomically acceptable salt-forming cation. In various preferred embodiments, $R^3$ is C$_1$-C$_8$ alkyl and more preferably methyl or ethyl. In other embodiments, $R^3$ is hydrogen. In still other embodiments, $R^3$ is a salt-forming ammonium cation.

Further, in various preferred embodiments, $R^1$ and $R^2$ are each hydrogen and $R^3$ is ethyl. In other preferred embodiments, $R^1$ is hydrogen, $R^2$ is —C(O)R$^4$, $R^3$ is ethyl, and $R^4$ is hydrogen. In still other preferred embodiments, $R^2$ is —C(O)$R^4$ and $R^1$, $R^3$, and $R^4$ are each hydrogen.

$R^1$ and $R^2$ may be part of a heterocyclic ring. For example, in certain embodiments, when $R^1$ is —C(O)$R^4$ and $R^2$ is —C(O)$R^5$, $R^4$ and $R^5$ may be bonded to form a heterocyclic ring. In various other embodiments, when $R^1$ and $R^2$ are each —C(O)$R^4$, $R^1$ and $R^2$ may be bonded to form a cyclic imide.

The nitrile-containing substrate as described above may be produced according to various processes. For example, in one process, acrolein is reacted with a phosphinate compound of Formula II,

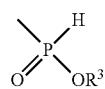

Formula II thereby forming a compound of Formula III

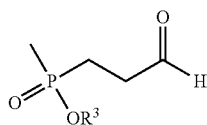

Formula III wherein $R^3$ in Formula II and Formula III is defined as described above for Formula I.

Further in accordance with these processes, compounds of Formula III are reacted with a cyanide source (e.g., NaCN) and an ammonia source according to a Strecker synthesis to form a nitrile-containing substrate of Formula IV, which proceeds according to the following reaction:

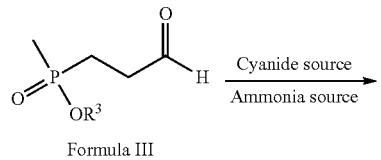

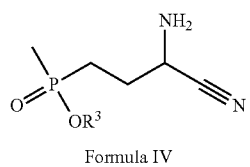

Formula IV wherein $R^3$ in Formula III and Formula IV is defined as described above for Formula I.

The nitrile-containing substrate of Formula IV produced by the Strecker synthesis can then be enzymatically hydrolyzed according to the process of the present invention by contacting in a reaction mixture (e.g., an aqueous medium) the nitrile-containing substrate (Formula IV) with an enzyme capable of catalyzing the hydrolysis of —CN to —COX, wherein X is —OH or —NH$_2$. In various embodiments, the enzymatic hydrolysis of the nitrile-containing substrate forms a phosphinothricin product.

Additionally or alternatively, the nitrile-containing substrate produced from the above Strecker synthesis (Formula IV) may be subjected to further reaction (e.g., alkylation or formylation) wherein, for example, at least one hydrogen of the primary amine group may be substituted. In various embodiments the substrate of Formula IV is further reacted with one or more formylation reagents to form an N-formyl substrate according to the following reaction:

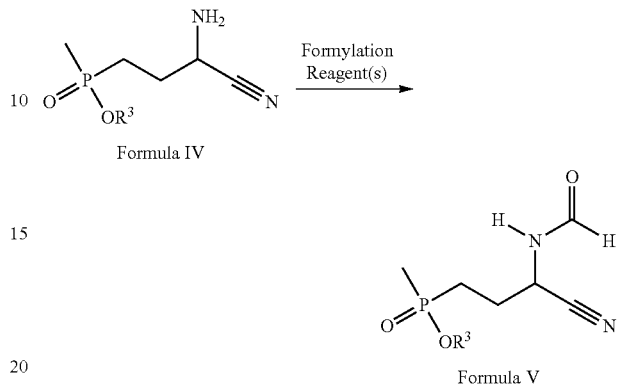

Formula V wherein $R^3$ in Formula IV and Formula V is defined as described above for Formula I.

A number of different formylation reagents may be used in this reaction. Typically, the one or more formylation reagents are selected from the group consisting of formic acid, acetic anhydride, ethyl formate, N-formyl benzotriazole, dichloromethane, and combinations thereof. In various embodiments, the one or more formylation reagents include formic acid and acetic anhydride. In various other embodiments, the one or more formylation reagents include ethyl formate. In still further embodiments, the one or more formylation reagents include N-formyl benzotriazole and dichloromethane.

Generally, regardless of the particular formylation reagents, the formylation reaction temperature is from about 0° C. to about 100° C., preferably from about 0° C. to about 50° C., and more preferably from about 0° C. to about 20° C.

II. Enzymatic Hydrolysis

Generally in accordance with the present invention, nitrile-containing substrates of Formula I may be contacted in a reaction mixture with an enzyme capable of catalyzing the hydrolysis of —CN to —COX, wherein X is —OH or —NH$_2$, thereby forming a phosphinothricin product or precursor thereof having the structure of Formula VI

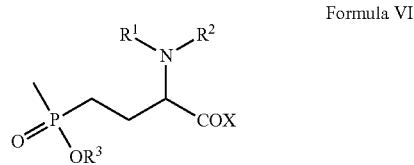

Formula VI wherein X is either —OH or —NH$_2$ and $R^1$, $R^2$, and $R^3$ are defined as described above for Formula I. In various preferred embodiments, X is —OH. In various other embodiments, X is —NH$_2$.

Typically, the reaction mixture comprises an aqueous medium. In various embodiments, the reaction mixture comprises an organic solvent. Suitable organic solvents include, for example, various aqueous miscible solvents known in the art, such as acetone, methyl-ethyl ketone, alcohols (e.g., methanol, ethanol, butanol, etc.), acetonitrile, methylene chloride, dioxane, tetrahydrofuran, dimethyl formamide, dimethyl sulfoxide, pyridine, substituted pyridines, etc. Aqueous/organic mixtures (volume/volume) may contain as low as about 1% v/v water or up to about 95% v/v water (e.g., between about 5% v/v to about 90% v/v water).

Additionally or alternatively, the reaction mixture may comprise an aqueous immiscible solvent that provides a biphasic reaction mixture. These aqueous immiscible solvents include, for example, various ethers (e.g., diethyl, di-isopropyl, methyl-tert-butyl, etc.), esters (e.g., ethyl acetate, butyl acetate, propyl acetate, etc.), and substituted benzenes (e.g., toluene, ethylbenzene, xylene, etc.).

When $R^1$ or $R^2$ are each hydrogen and X is —OH, the compound of Formula VI is a phosphinothricin product (i.e., the acid or a salt or ester thereof). A salt of Formula VI is formed when either $R^3$ or the —OH group (when X is —OH) is replaced with an agronomically acceptable salt-forming cation. Additionally or alternatively, a di-salt of Formula VI may be formed when $R^3$ and the —OH group (when X is —OH) are replaced with an agronomically acceptable salt-forming cation. An ester of Formula VI is formed when either $R^3$ or the —OH group (when X is —OH) is replaced with a substituted or unsubstituted $C_1$-$C_8$ alkyl or a substituted or unsubstituted aryl. Similarly, a di-ester of Formula VI may be formed when $R^3$ and the —OH group (when X is —OH) are replaced with a substituted or unsubstituted $C_1$-$C_8$ alkyl or a substituted or unsubstituted aryl.

Generally, the phosphinothricin product or precursor thereof of Formula VI may be further hydrolyzed when at least one $R^1$, $R^2$, or $R^3$ are not hydrogen.

In various other embodiments, when X is —$NH_2$, the compound of Formula VI may be further hydrolyzed to convert the —$NH_2$ to —OH. Hydrolysis of —$NH_2$ may be conducted according to conventional methods known in the art. Hydrolysis may also be accomplished by enzymatic means. For example, an enzyme comprising an amidase may be used to catalyze the hydrolysis of —$NH_2$ to —OH in accordance with the present invention.

In various preferred embodiments, a phosphinothricin product or precursor thereof may be prepared from the above-described N-formyl substrate (Formula V) in accordance with the present invention by contacting in a reaction mixture the N-formyl substrate with an enzyme capable of catalyzing the hydrolysis of —CN to —COX, wherein X is either —OH or —$NH_2$, thereby forming a compound of Formula VII or a salt or ester thereof Formula VII

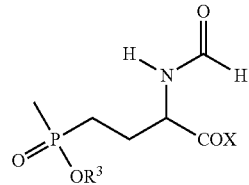

wherein $R^3$ is defined as described above for Formula I. The formyl group of Formula VII is then hydrolyzed to form a phosphinothricin product (i.e., the acid or a salt or ester thereof).

In general, the reactions described above may be conducted in either a batch, semi-batch or continuous reactor system. The reactor system may include one or more stirred tank reactors, fluidized bed reactors, or plug flow reactors. Moreover, the reactors may be configured in series or in parallel. In various embodiments, the enzymatic hydrolysis of the nitrile-containing substrate is conducted in one or more stirred tank reactors.

Generally, the enzymatic hydrolysis is conducted at a temperature of at least about 10° C. or at least about 20° C. Typically, the enzymatic hydrolysis is conducted at a temperature from about 10° C. to about 100° C., more typically from about 20° C. to about 80° C., from about 20° C. to about 60° C., or from about 20° C. to about 40° C. (e.g., about 30° C.).

Typically, the enzymatic hydrolysis is conducted at a pressure of at least about 100 kiloPascals (kPa). For example, the enzymatic hydrolysis is typically conducted at a pressure from about 100 kPa to about 1000 kPa, more preferably from about 100 kPa to about 500 kPa, and still more preferably from about 100 kPa to about 200 kPa (e.g., from about 100 kPa to about 150 kPa).

Generally, the pH of the reaction mixture is at least about 2. In various embodiments, the pH of reaction mixture is from about 2 to about 10 and preferably from about 4 to about 8.

Production of a phosphinothricin product or precursor thereof in accordance with the present invention produces both D-and L-stereoisomers. As noted, various embodiments of the present invention are directed to enzymatic hydrolysis processes for the preparation of phosphinothricin products or precursors thereof that are believed to be stereoselective, preferentially producing L-phosphinothricin products and precursors thereof. These processes are believed to generally comprise dynamic kinetic resolution (DKR) of D-stereoisomers of Formula I, which results in the preferential preparation of the L-stereoisomers of the phosphinothricin products or precursors thereof. Without being bound to a particular theory, it is currently believed that the presence of the enzyme may reduce the free energy of reaction of the L-stereoisomer of Formula I such that its hydrolysis to the resulting carboxylic acid or amine proceeds at a greater rate than the competing hydrolysis of the D-stereoisomer. Additionally or alternatively, without being bound by theory, it is also currently believed that the enzyme may preferentially react with the L-stereoisomer of Formula I such that hydrolysis of the preferred L-stereoisomer of Formula I proceeds at a greater rate than hydrolysis of D-stereoisomer In various embodiments, it is believed that reaction conditions and/or components of the reaction mixture may promote dynamic kinetic resolution, resulting in the isomerization of the alpha amine group according to the following scheme:

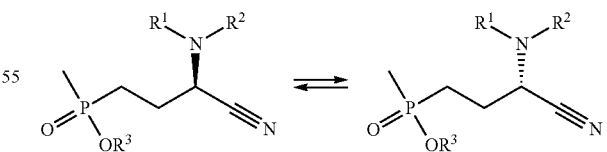

wherein $R^1$, $R^2$, and $R^3$ are defined as described above for Formula I. Reaction conditions that may promote the above isomerization include the pH (e.g., within from about 2 to about 10) and temperature (within from about 20° C. to about 60° C.) of the reaction mixture. Thus, the processes of the present invention may include adjusting and/or maintaining either or both of these conditions within a preferred range. Additionally or alternatively, various components may be added to the reaction mixture to promote the above isomerization. These compounds are believed to include one or more metals, organic compounds (e.g., aldehydes), and/or organic bases (e.g., pyridine, triethyl amine, etc.).

The processes of the present invention typically provide a product mixture, or slurry comprising D-and L-stereoisomers of the phosphinothricin product or precursor thereof. Regardless of the precise mechanism by which it occurs, it is further believed that the processes of the present invention result in a product mixture containing an excess of the L-phosphinothricin product or precursor thereof over D-phosphinothricin product or precursor thereof. That is, typically, the weight ratio of the L-phosphinothricin product or precursor thereof to the D-phosphinothricin product or precursor thereof is believed to be greater than about 1:1 (e.g., greater than 1:1), greater than about 2:1 or greater than about 5:1. Preferably, the weight ratio of the L-phosphinothricin product or precursor thereof to the D-phosphinothricin product or precursor thereof in the product mixture is believed to be greater than about 10:1, or even greater than about 20:1.

The enzymatic hydrolysis processes of the present invention are also believed to provide a higher yield of the L-phosphinothricin product or precursor thereof. Typically, the yield of the L-phosphinothricin product or precursor thereof is believed to be greater than about 10%, greater than about 20%, greater than about 30%, greater than about 40%, or greater than about 50%. Preferably, the yield of the L-phosphinothricin product or precursor thereof is believed to be greater than about 60% greater than about 70%, greater than about 80%, or greater than about 90%.

III. Product Recovery

The phosphinothricin product or precursor thereof may be recovered from the product mixture or slurry by one or more conventional methods known in the art including, for example, precipitation, solvent extraction, and chromatographic separation. In those processes in which precipitation is utilized, the pH is typically adjusted by addition of acid or base to precipitate the zwitterions or by addition of a salt, such as ammonia which forms the ammonium salt. Additionally or alternatively, phosphinothricin product may be recovered from the product mixture utilizing chromatographic separation methods including, for example, cation exchange chromatography in which the product mixture is contacted with a bed of cation exchange resin.

The phosphinothricin product or precursor thereof produced by the processes of the present invention may be subjected to further processing including purification, concentration, drying, granulation, etc., according to means known in the art.

IV. Herbicidal Formulations

The phosphinothricin products produced by the processes of the present invention are useful as herbicidal agents. Phosphinothricin products (i.e., glufosinate or salts or esters thereof) prepared and recovered in accordance with the present invention may be included in herbicidal formulations along with various other components in accordance with methods known in the art. Typically, glufosinate is formulated in the form of its ammonium salt. Formulations of glufosinate or its salts or esters thereof may include other components such as surfactants, stabilizers, and/or co-herbicides, fungicides, or pesticides.

V. Enzymes

Enzymes that are capable of catalyzing the hydrolysis of —CN to —COX, wherein X is either —OH or —$NH_2$ are suitable for use in the present invention. Suitable examples of such enzymes include, for example, nitrilases, nitrile hydratases, mixtures of nitrile hydratases and amidases, and mixtures thereof. Nitrilases are capable of catalyzing the hydrolysis of —CN to —OH. Nitrile hydratases are capable of catalyzing the hydrolysis of —CN to —$NH_2$, which then can be subsequently hydrolyzed to —OH by either conventional hydrolysis or by enzymatic hydrolysis. Enzymes useful for catalyzing the hydrolysis of —$NH_2$ to —OH comprise amidases. Accordingly, a mixture of nitrile hydratase and amidase is capable of hydrolyzing —CN to —OH.

Thus, in various embodiments of the process described herein, the process comprises the use of a nitrilase. In other embodiments, the process comprises the use of a nitrile hydratase. In still other embodiments, the process comprises the use of a mixture of nitrile hydratase and amidase. In various other embodiments, the process comprises the use of a mixture of nitrilase and nitrile hydratase. Still further embodiments, the process comprises the use of a mixture of nitrilase, nitrile hydratase, and amidase.

Suitable enzymes that are capable of catalyzing the hydrolysis of —CN to —COX, wherein X is either —OH or —$NH_2$ may be obtained from any number of sources or by any number of methods. For example, the enzymes may be obtained from a source organism, such as a eukaryote or prokaryote which naturally expresses or produces the enzyme (i.e., a source organism to which the enzyme is endogenous). Examples of suitable eukaryotes include species from the genera *Arabidopsis*, *Nicotiana*, and *Brassica*, and include the particular species *A. thaliana*, *N. tabacum*, *B. campestris*, *B. napaus*, *Aspergillus*, *Trichoderma*, *Saccharomyces*, *Pichia*, *Candida*, and *Hansenula*. Examples of suitable prokaryotes include species from the genera of *Salmonella*, *Bacillus*, *Acinetobacter*, *Zymomonas*, *Agrobacterium*, *Erythrobacter Chlorobium*, *Chromatium*, *Flavobacterium*, *Cytophaga*, *Rhodobacter*, *Rhodococcus*, *Streptomyces*, *Brevibacterium*, *Corynebacteria*, *Mycobacterium*, *Deinococcus*, *Escherichia*, *Erwinia*, *Pantoea*, *Pseudomonas*, *Sphingomonas*, *Methylomonas*, *Methylobacter*, *Methylococcus*, *Methylosinus*, *Methylomicrobium*, *Methylocystis*, *Methylobacterium*, *Alcaligenes*, *Synechocystis*, *Synechococcus*, *Anabaena*, *Thiobacillus*, *Methanobacterium*, *Klebsiella*, *Myxococcus*, and *Staphylococcus*, and include the particular species of *P. putida*, *P. fluorescens*, *R. rhodochrous*, *R. erythropolis*, *R. equi*, *R. chloroaphis*, *A. faecalis*, and *E. coli*.

Alternatively, the enzyme may be obtained from a source organism that has been manipulated to produce the enzyme (i.e., a source organism to which the enzyme is exogenous). That is to say, the enzyme of interest may be produced in heterologous host cells, particularly microbial host cells.

Preferred heterologous microbial host cells for expression of targeted enzymes are microbial hosts that can be found broadly within the fungal or bacterial families and which grow over a wide range of temperature, pH values, and solvent tolerances. For example, any bacteria, yeast, and filamentous fungi will be suitable hosts for expression of the genes encoding the enzyme of interest. Because transcription, translation, and the protein biosynthetic apparatus are the same irrespective of the cellular feedstock, targeted genes are expressed irrespective of carbon feedstock used to generate cellular biomass. Large-scale microbial growth and functional gene expression may utilize a wide range of simple or complex carbohydrates, organic acids and alcohols, and saturated hydrocarbons such as methane, or carbon dioxide in the case of photosynthetic or chemoautotrophic hosts. However, the targeted genes may be regulated (up or down), repressed or depressed by specific growth conditions, which may include the form and amount of nitrogen, phosphorus, sulfur, oxygen, carbon or any trace micronutrient including small inorganic ions. In addition, the regulation of targeted genes may be achieved by the presence or absence of specific regulatory molecules that are added to the culture and are not typically considered nutrient or energy sources.

Prokaryotic, and more preferably microbial, expression systems and expression vectors containing regulatory sequences that direct high level expression of foreign proteins, as well as eukaryotic expression systems and expression vectors containing regulatory sequences that direct high level expression of foreign proteins, are well known to those skilled in the art. Any of these could be used to construct genes for expression of the present nitrilase, nitrile hydratase, and/or amidase enzymes. These genes could then be introduced into appropriate microorganism cells via transformation to provide high-level expression of the enzymes.

For example, introduction of targeted genes encoding the instant targeted enzymes (e.g., nitrilase, nitrile hydratase, and/or amidase enzymes) under the control of the appropriate promoter will demonstrate increased nitrile to amide and/or carboxylic acid conversion. It is contemplated that it will be useful to express the targeted genes both in a natural host cell, as well as in a heterologous host cell. Introduction of targeted genes into native hosts will result in altered levels of existing nitrilase, nitrile hydratase and amidase activity. Additionally, targeted genes may also be introduced into non-native hosts where an existing nitrile-amide-carboxylic acid pathway may be manipulated.

Vectors or cassettes, preferably plasmids, useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the targeted gene which harbors transcriptional initiation controls and a region 3' of the DNA fragment which controls transcriptional termination. It is most preferred that both control regions are derived from genes homologous to the transformed host cell, although it is to be understood that such control regions need not be derived from the genes native to the specific species chosen as a production host.

Initiation control regions or promoters, which are useful to drive expression of the instant open reading frame (ORF) in the desired microbial host cell are numerous and familiar to those skilled in the art. Virtually any promoter capable of driving these genes is suitable for the present invention, including, but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*. Additionally, the deoxy-xylulose phosphate synthase or methanol dehydrogenase operon promoter (Springer et al., FEMS Microbiol Lett 160:119 124 (1998)), the promoter for polyhydroxyalkanoic acid synthesis (Foellner et al., Appl. Microbiol. Biotechnol. 40:284 291 (1993)), promoters identified from native plasmids in methylotrophs (EP 296484), promoters identified from methanotrophs (WO 2004/037998), and promoters associated with antibiotic resistance (e.g., kanamycin (Springer et al., supra; Ueda et al., Appl. Environ. Microbiol. 57:924 926 (1991)) or tetracycline (U.S. Pat. No. 4,824,786)) are suitable for expression of the present coding sequences, especially in C1 metabolizers.

The vector or expression cassette comprising the targeted gene and a promoter can also typically include a marker gene which confers a selectable phenotype on the host cell. For example, the marker can encode antibiotic resistance, such as resistance to kanamycin, ampicillin, chloramphenicol, etc. In addition, plasmids can be maintained by auxotrophic methods resulting from the deletion of an essential gene from the host strain and complementing it by inclusion of the essential gene in plasmid containing the targeted gene.

Methods of manipulating genetic pathways are common and well known in the art. Selected genes in a particular pathway may be up-regulated or down-regulated by a variety of methods.

Specific genes may be up-regulated to increase the output of the desired nitrilase, nitrile hydratase, and amidase enzymes. For example, additional copies of the targeted genes (i.e., the genes encoding the desired enzymes) may be introduced into the host cell on multicopy plasmids such as pBR322, pUC and the like. Alternatively, the genes may be modified so as to be under the control of non-native promoters. Where it is desired that a pathway operate at a particular point in a cell cycle or during a fermentation run, regulated or inducible promoters may be used to replace the native promoter of the target gene. Similarly, in some cases the native or endogenous promoter may be modified to increase gene expression. For example, endogenous promoters can be altered in vivo by mutation, deletion, and/or substitution (see, Kmiec, U.S. Pat. No. 5,565,350; Zarling et al., WO 93/22443).

Vectors and constructs can be introduced into the genome of a desired host, such as, for example, either yeast or microbial host, by a variety of conventional techniques. For reviews of such techniques see, for example, Weissbach & Weissbach Methods for Plant Molecular Biology (1988, Academic Press, N.Y.) Section VIII, pp. 421-463; and Grierson & Corey, Plant Molecular Biology (1988, 2d Ed.), Blackie, London.

The enzymes useful in the present invention may be used in an isolated or purified form or in a whole cell form. Thus, the enzymes may be isolated from the source or host cell and used directly in an enzymatic hydrolysis by combining the enzyme with the nitrile-containing substrate, for instance, in a reaction mixture. Likewise, the enzymes may be synthesized in a purified form by means of peptide syntheses well known in the art. Thus, in one embodiment of the process described herein, the process comprises the use of an isolated or purified form of a nitrilase, nitrile hydratase, mixture of nitrilase and amidase, or mixtures thereof. In another embodiment, the process comprises the use of an isolated or purified form of a nitrilase, a nitrile hydratase, a mixture of nitrile hydratase and amidase, or mixtures thereof, and a co-factor for the activation or proper or sustained function of the enzyme. In various embodiments, the isolated or purified form of the enzyme is a nucleic acid molecule encoding a nitrilase capable of catalyzing the hydrolysis of —CN to —COX wherein X is —OH or —$NH_2$ and the molecule comprises a nucleotide sequence selected from the group consisting of SEQ ID NO: 1, SEQ ID NO: 2, SEQ ID NO: 3, SEQ ID NO: 4, SEQ ID NO: 5, and SEQ ID NO: 6.

In other embodiments, the nucleic acid molecule is contained in a vector. In various embodiments, the vector comprises a nucleic acid molecule selected from the group consisting of SEQ ID NO: 1, SEQ ID NO: 2, SEQ ID NO: 3, SEQ ID NO: 4, SEQ ID NO: 5, and SEQ ID NO: 6. In other embodiments, the vector may be the plasmid pSEA99 represented by SEQ ID NO: 7 or the plasmid pSEA100 represented by SEQ ID NO: 8. The nucleic acid molecules of the present invention may also be in a host cell. Thus, in various embodiments the host cell comprises a nucleic acid molecule selected from the group consisting of SEQ ID NO: 1, SEQ ID NO: 2, SEQ ID NO: 3, SEQ ID NO: 4, SEQ ID NO: 5, and SEQ ID NO: 6. In other embodiments, the host cell comprises a vector comprising a nucleic acid molecule selected from the group consisting of SEQ ID NO: 1, SEQ ID NO: 2, SEQ ID NO: 3, SEQ ID NO: 4, SEQ ID NO: 5, and SEQ ID NO: 6. In particular embodiments, the vector may be the plasmid pSEA99 represented by SEQ ID NO: 7 or the plasmid pSEA100 represented by SEQ ID NO: 8.

The nucleic acid molecules of the present invention encode nitrilase proteins. In various embodiments, the protein comprises a polypeptide sequence encoded by the nucleic acid molecule selected from the group consisting of SEQ ID NO: 1, SEQ ID NO: 2, SEQ ID NO: 3, SEQ ID NO: 4, SEQ ID NO: 5, and SEQ ID NO: 6.

In another embodiment, the process comprises the use of an enzyme encoded by a nucleotide sequence of SEQ ID NO: 1, SEQ ID NO: 2, SEQ ID NO: 3, SEQ ID NO: 4, SEQ ID NO: 5, or SEQ ID NO: 6. In certain embodiments, the enzyme is encoded by a nucleotide sequence contained in a vector, and in particular the plasmid pSEA99 represented by SEQ ID NO: 7 or the plasmid pSEA100 represented by SEQ ID NO: 8.

Alternatively, the enzymes may be utilized as part of a whole cell enzymatic hydrolysis. In such an instance, the source or host organism containing or producing the enzyme of interest is combined directly with the nitrile-containing substrate, for instance, in a reaction mixture. Use of a whole cell procedure is generally preferred, as this typically negates the necessity of providing any additional co-factors needed for activation of and/or proper and sustained enzyme function, those co-factors being present in or produced by the source or host cell. In addition, operational steps in the lysis and enzyme isolation are avoided thereby reducing the downstream processing costs. Thus, in various embodiments of the process described herein, the process comprises the use of a whole cell procedure comprising combining or contacting the nitrile-containing substrate with a source or host cell that contains, produces, or expresses a nitrilase, nitrile hydratase, and/or amidase.

Various enzyme formulations can be used to perform the enzymatic hydrolysis in any of the above reaction mixtures (e.g., an aqueous reaction mixture or aqueous/organic mixture). These include cell free enzyme lysates, intact microorganisms that contain native levels of the desired activity, or recombinant microorganisms that over express a foreign (or native) gene from a plasmid or from a genomic insertion.

The enzymes can be used in unmodified forms as in the case of crude protein mixtures containing the desired protein, semi-purified protein formulations, or in immobilized forms. Protein immobilization can be done according to various published methods known to those skilled in the art including, for example, covalent attachment in various solid supports, entrapment in polymers by copolymerization with alginate, carrageenan, or other synthetic polymers, as well as cross-linking using various agents such as glutaraldehyde for the formation of cross-linked enzyme aggregates (CLEAs) (See, for example, "Immobilization of Enzymes and Cells" $2^{nd}$ Ed, Edited Jose M. Guisan, 2006 Humana Press; Brady, D. Jordan, J. *Biotechnol. Lett.* 2009, 31, 1639; Sheldon, R. A. *Adv. Synth. Catal.* 2007, 349, 1289), the entire content of each of which is hereby incorporated herein by reference for all relevant purposes.

Similarly, whole cells containing the desired activity can be immobilized in various materials such as alginate, carrageenan, and other polymeric supports following methods described in the literature and known by those skilled in the art (See, for example, "Immobilization of Enzymes and Cells" $2^{nd}$ Ed, Edited: Jose M. Guisan, 2006 Humana Press; DiCosimo R. et al *Org. Proc. Res. Devel.* 2002, 6, 492; DiCosimo, R. et al *Adv. Synth. Catal.* 2008, 350, 1761), the entire content each of which is hereby incorporated herein by reference for all relevant purposes.

VI. Definitions

Unless otherwise indicated, the term "$C_1$-$C_8$ alkyl" as used herein contains from 1 to 8 carbon atoms in the principal chain. They may be straight or branched chain or cyclic and include methyl, ethyl, propyl, isopropyl, n-butyl, isobutyl, hexyl, 2-ethylhexyl, and the like.

The term "aryl" as used herein denotes optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

Alkyl and aryl groups can be substituted with at least one atom other than carbon, including moieties in which a carbon chain atom is substituted with a hetero atom such as nitrogen, oxygen, silicon, phosphorus, boron, sulfur, or a halogen atom. These substituents include, for example, hydroxy, nitro, amino, amido, nitro, cyano, sulfoxide, thiol, thioester, thioether, ester and ether.

The term "heterocyclic ring" as used herein denotes optionally substituted, fully saturated or unsaturated, monocyclic or bicyclic, aromatic or nonaromatic groups having at least one heteroatom in at least one ring (i.e., nitrogen), and preferably 5 or 6 atoms in each ring (e.g., cyclic imides).

The following non-limiting examples are provided to further illustrate the present invention.

EXAMPLES

Plasmids were prepared by cloning synthetic genes into the commercial plasmid vector pJExpress 401 (DNA2.0) (FIG. 1). For both pSEA099 and pSEA100 the synthetic genes were designed to optimize codon usage for expression in *E. coli*. The synthetic genes were constructed and cloned into the pJexpress vector by DNA2.0. The cloning was performed by digesting the synthetic gene with NdeI (5') and Hind III (3') and ligating at the same sites in the pJexpress vector. The plasmid sequences for pSEA099 and pSEA100 are SEQ ID NOS: 7 and 8, respectively. The plasmids also contain a pUC origin for replication, Kanamycin resistance, and LacI gene for controlling expression with isopropyl β-D-1-thiogalactopyranoside (IPTG).

Example 1

Preparation of Nitrilase Protein for Reaction with N-Formyl Nitrile Phosphinic Ester A 10 mL LB/Kanamycin (50 µg/mL Kanamycin) solution was inoculated with a colony of *E. coli* BL21/pSEA100. After culturing for 16 hours at approximately 37° C., the culture was transferred to a 2.8 L baffled Erlenmeyer flask containing 1 L of LB/Kan. Cells were incubated at 37° C. in a shake oven (200 rpm shaking) to a cell density of $OD_{600}$=0.8 before decreasing the temperature to approximately 25° C. and adding 1 mM of IPTG. After 16 hours of growth following IPTG induction, cells were harvested via centrifugation at 7,000×g for about 20 minutes. The cell pellet was resuspended in 50 mL assay buffer (50 mM potassium phosphate pH 7.5, 1 mM of dithiothreitol (DTT)) and cells were lysed by sonication. Cell debris was removed via centrifugation at 35,000×g for 60 minutes.

The previous clear lysate (approximately 20 mg/mL total protein, >50% nitrilase) was brought to 20% saturation with ammonium sulfate. After stirring on ice for about 2 hours, the precipitated protein was removed by centrifugation at 35,000×g for 60 minutes. Ammonium sulfate was added to the remainder of the supernatant incrementally to 30% saturation while stirring on ice for 2 hours. The precipitated protein (obtained by centrifugation at 35,000×g for 60 minutes) was redissolved in assay buffer to a 20 mg/mL protein concentration (>80% nitrilase in this solution).

Example 2

Reaction of N-Formyl Nitrile Phosphinic Ester (S) to N-Formyl Acid Phosphinic Ester (P)

The reaction mixture was prepared by mixing 800 μL of assay buffer with 100 μL of the nitrilase solution recovered as described in Example 1 (giving a total protein concentration of 2 mg/mL) and 100 μL of 20 mg/mL N-formyl nitrile solution (dissolved in assay buffer). After stirring at approximately 30° C. for 28 hours, HPLC analysis identified a 24% conversion (at 8 hours an 8% conversion was determined). The peak at about 19 minutes was assigned as the product by comparison with authentic standards and by HPLC analysis.

Example 3

HPLC Analysis of the Reaction Progress

A crude sample from the reaction mixture prepared as described in Example 2 was filtered and 10 μl was injected on a Phenomenex Prodigy 5μ ODS (2) Column (250 mm×4.6 i.d.) equilibrated in 5% methanol/95% (0.1% trifluoroacetic acid (TFA) in water). The column ran isocratically at 1 mL/min. Both starting material and products were analyzed at 210 nm.

Figure 2:
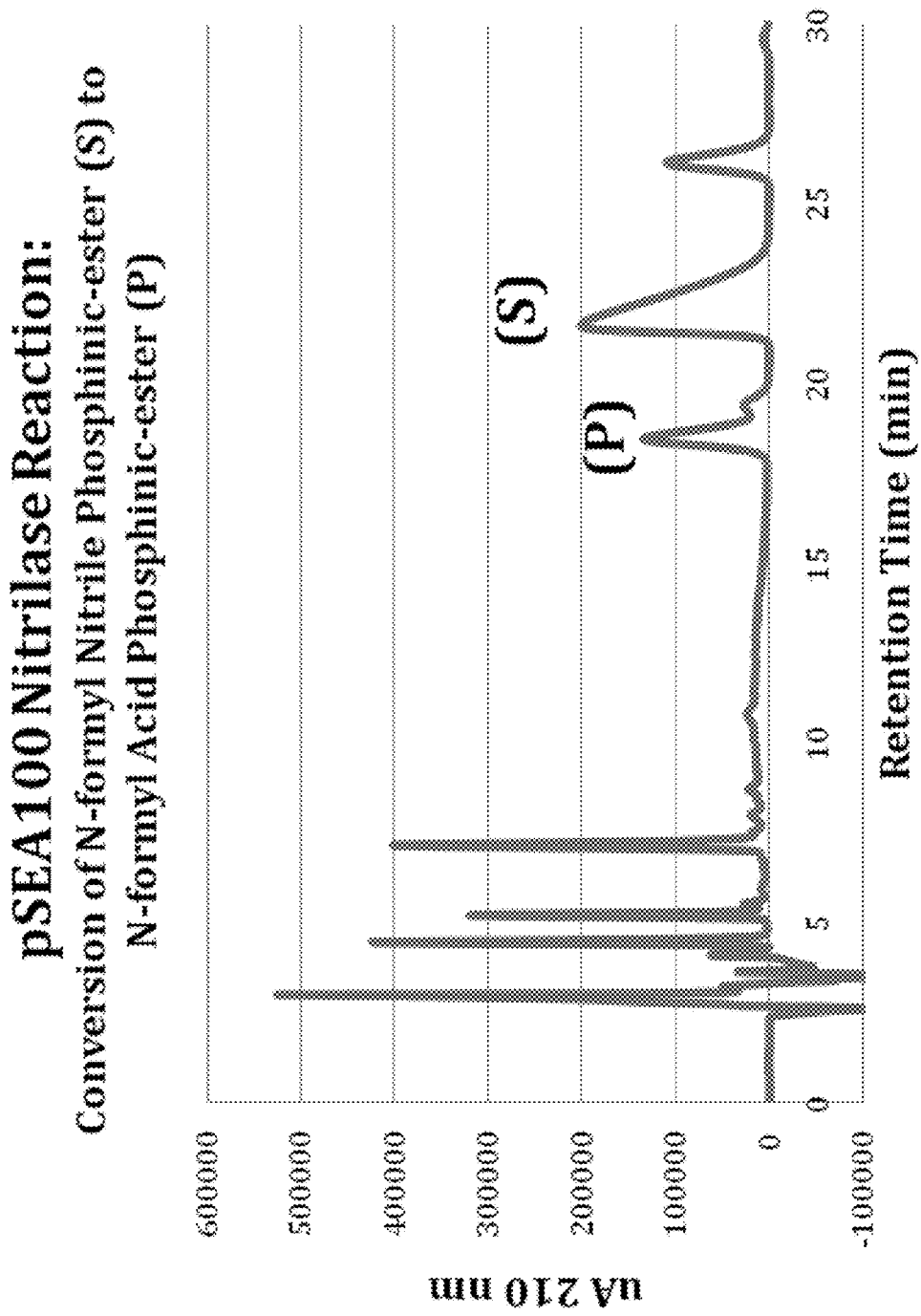
FIG. 2 shows high performance liquid chromatography (HPLC) results for the conversion of N-formyl nitrile phosphinic ester to N-formyl acid phosphinic ester determined as described in Example 3.

FIG. 2 provides the HPLC analytical results for the reaction mixture. The results show the formation of the n-formyl acid phosphinic ester product as indicated by the peak labeled "(P)".

Example 4

Preparation of Nitrilase Protein for Reaction with Ethyl 3-Amino-3-CYANOPROPYL(Methyl)Phosphinate A 5 mL LB/Kanamycin (50 μg/mL Kanamycin) solution was inoculated from a frozen glycerol stock of E. coli BL21/pSEA100. After 16 hours of growth at approximately 37° C., 2.5 mL of the culture was transferred to a 1 L baffled shake flask containing 200 mL of LB/Kan and 5 g of glucose. Cells were incubated at approximately 37° C. in a shake oven (200 rpm shaking) to a cell density of $OD_{600}=1.0$ before decreasing the temperature to 25° C. and adding 1 mM of IPTG. After 16 hours of growth following the IPTG induction, cells were harvested via centrifugation at 7,000×g for 20 minutes. The cell pellet was resuspended in 10 mL assay buffer (10 mM potassium phosphate pH 7.5, 1 mM DTT) and cells were lysed by sonication. Cell debris was removed via centrifugation at 35,000×g for 20 minutes and 3 mL of 80% glycerol was added to the clear lysate. The cell lysate was stored at 4° C. for 48 hours.

Example 5

Reaction of Ethyl 3-Amino-3-Cyanopropyl(Methyl)Phosphinate (S) to N-Formyl Acid Phosphinic ESTER (P)

In a 5 mL test tube 0.6 mL assay buffer (10 mM potassium phosphate pH 7.5, 1 mM DTT), 10 mg of free aminonitrile substrate (i.e., ethyl 3-amino-3-cyanopropyl(methyl)phosphinate) and 0.4 mL of the pSEA100 lysate prepared as described above in Example 1 were mixed. The progress of the reaction was followed by HPLC analysis after fluorenylmethyloxycarbonyl (FMOC) derivatization (see below) of the crude reaction mixture. After stirring at 30° C. for 24 hours, a conversion to glufosinate of approximately 21% was achieved.

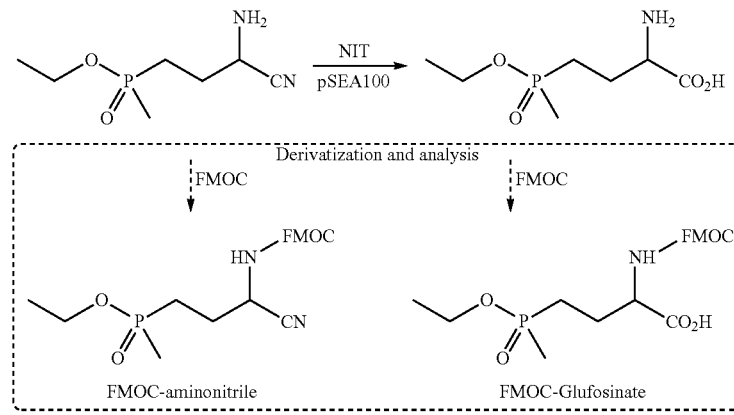

Example 6

FMOC Derivatization and Analysis

A 100 μL aliquot of the reaction mixture prepared as described in Example 5 was transferred to a clean 5 mL test tube and quenched with 100 μL acetonitrile. The resulting reaction mixture was mixed with 50 μL of FMOC solution (52 mg fluorenylmethyloxycarbonyl chloride dissolved in 1 mL acetonitrile) and 2 drops of saturated sodium bicarbonate. This solution was stirred for 30 minutes at 30° C., converting unreacted aminonitrile and glufosinate product to their corresponding FMOC derivatives. The FMOC derivatized mixture was filtered and analyzed on a Phenomenex Prodigy 5μ ODS (2) Column (250 mm×4.6 i.d.) equilibrated in 40% water/60% (0.1% TFA in methanol). The column ran isocratically at 1 mL/min. Both starting material and products were analyzed at 254 nm; the peak at 8.7 min was assigned as FMOC-Glufosinate and the peak at 11.9 min was assigned as FMOC-aminonitrile.

Starting material and product were compared with authentic standards. Under these non-chiral analysis conditions all diastereomers of starting material and product elute in a single peak.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying figures shall be interpreted as illustrative and not in a limiting sense. Having described the invention in detail, it will be apparent that modifications and variations are possible without departing from the scope of the invention defined in the appended claims.

What is claimed is:

1. A process for the preparation of a phosphinothricin product or precursor thereof, the process comprising:
   (a) reacting a compound of Formula III

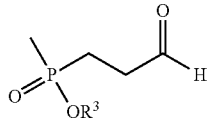

Formula III with a cyanide source and an ammonia source, thereby forming a nitrile-containing substrate of Formula IV;

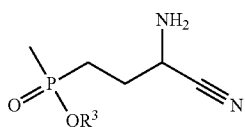

Formula IV (b) reacting the nitrile-containing substrate of Formula IV with one or more formylation reagents, thereby producing an N-formyl substrate of Formula V;

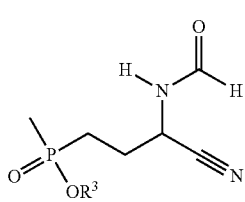

Formula V (c) contacting in a reaction mixture the N-formyl substrate of Formula V with an enzyme capable of catalyzing the hydrolysis of —CN to —COX, wherein X is either —OH or —NH$_2$, thereby producing a compound of Formula VII

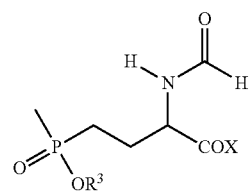

Formula VII wherein $R^3$ is hydrogen, substituted or unsubstituted $C_1$-$C_8$ alkyl, substituted or unsubstituted aryl, or an agronomically acceptable salt-forming cation; and (d) hydrolyzing the compound of Formula VII to form a phosphinothricin product or precursor thereof.

2. The process as set forth in claim 1 wherein the one or more formylation reagents are selected from the group consisting of formic acid, acetic anhydride, ethyl formate, N formyl benzotriazole, dichloromethane, and combinations thereof.

3. The process as set forth in claim 1 wherein the one or more formylation reagents comprise formic acid and acetic anhydride.

4. The process as set forth in claim 1 wherein the one or more formylation reagents comprise ethyl formate.

5. The process as set forth in claim 1 wherein the one or more formylation reagents comprise N formyl benzotriazole and dichloromethane.

6. The process as set forth in claim 1 wherein the formylation reaction is conducted at a temperature from about 0° C. to about 100° C.

7. The process as set forth in claim 1 wherein $R^3$ is substituted or unsubstituted $C_1$-$C_8$ alkyl, substituted or unsubstituted aryl, or an agronomically acceptable salt-forming cation.

8. A nitrile-containing compound having the structure of Formula V

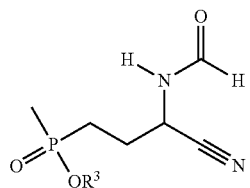
Formula V
wherein R³ is hydrogen or an agronomically acceptable salt-forming cation.
9. The nitrile-containing compound as set forth in claim 8 wherein R³ is hydrogen.
* * * * *